(12) United States Patent
Gorelik et al.

(10) Patent No.: US 10,618,942 B2
(45) Date of Patent: Apr. 14, 2020

(54) UBIQUITIN VARIANT MODULATORS OF SCF E3 LIGASES AND THEIR USES

(71) Applicant: The Governing Council of the University of Toronto, Toronto (CA)

(72) Inventors: Maryna Gorelik, Toronto (CA); Sachdev Sidhu, Toronto (CA)

(73) Assignees: Sachdev Sidhu, Toronto (CA); Maryna Gorelik, Toronto (CA)

( * ) Notice: Subject to any disclaimer, the term of this patent is extended or adjusted under 35 U.S.C. 154(b) by 46 days.

(21) Appl. No.: 15/436,337

(22) Filed: Feb. 17, 2017

(65) Prior Publication Data

US 2017/0321205 A1 Nov. 9, 2017

Related U.S. Application Data

(60) Provisional application No. 62/296,315, filed on Feb. 17, 2016.

(51) Int. Cl.
| | | |
|---|---|---|
| C07K 14/00 | (2006.01) | |
| C07H 21/04 | (2006.01) | |
| C12N 9/00 | (2006.01) | |
| C12N 15/10 | (2006.01) | |
| C07K 14/47 | (2006.01) | |
| G01N 33/50 | (2006.01) | |
| C07K 7/08 | (2006.01) | |

(52) U.S. Cl.
CPC ............. *C07K 14/47* (2013.01); *C07H 21/04* (2013.01); *C07K 14/00* (2013.01); *C12N 9/93* (2013.01); *C12N 15/1055* (2013.01); *C12N 15/1058* (2013.01); *C12Y 603/02019* (2013.01); *C07K 7/08* (2013.01); *G01N 33/5008* (2013.01); *G01N 2333/9015* (2013.01)

(58) Field of Classification Search
CPC ......... C07H 21/04; C07K 14/00; C07K 14/47
See application file for complete search history.

(56) References Cited

PUBLICATIONS

Uniprot entry for Q8C2K3_Mouse (Year: 2003).*

* cited by examiner

*Primary Examiner* — Jeremy C Flinders
(74) *Attorney, Agent, or Firm* — Clark & Elbing LLP

(57) ABSTRACT

The invention provides ubiquitin variants that specifically bind to SCF E3 ligases, and use of these variants to modulate the activity of SCF E3 ligases.

9 Claims, 8 Drawing Sheets

Specification includes a Sequence Listing.

| | Region 1 | Region 2 | Region 3 | IC$_{50}$ (nM) |
|---|---|---|---|---|
| | 6 7 9 10 | 36 42 44 46 47 48 49 | 66 68 70 71 72 73 74 75 76 | Skp1-F-box$^{Fbw7}$ |
| Library2 | K T A A | E I I S R K L | T R V L I F R G G | |
| Fw7.1 | - - - - | - - - - - - - | - - - - - - - - N | WB |
| Fw7.5 | - - - G | - V - - - - R | - - - - V - G R R | 45 ± 6 |
| Fw7.6 | - - - G | - - - - - - R | - - - - - - P S - | 80 ± 9 |
| Fw7.7 | - - - G | - R - A G R R | - - - Y V - - R - | 110 ± 20 |
| Fw7.8 | - - - G | - R - A G - - | - - - W F L - F V | 110 ± 30 |
| Fw7.9 | - - - G | - - - - - - R | - - - M V - S K - | 110 ± 10 |
| Fw7.10 | - - T G | - V L - - - V | - - - W L L - R - | 120 ± 50 |
| Fw7.11 | - - - - | G V - - K - R | - - - - - - - R - | 130 ± 20 |
| Fw7.12 | - - - - | - R - A G - R | - - - - L - - R E | 140 ± 10 |
| Fw7.13 | - - S G | G - L - - - R | - - - - - S - A | 170 ± 4 |
| Fw7.14 | - - - - | D V L R - - K | - - L W - V - R - | 170 ± 4 |
| Fw7.15 | - - - G | - - - - H M R | - - - - - S - - | 180 ± 20 |
| Fw7.16 | - - - G | G - L - - - P | - - - V V - - R - | 210 ± 20 |
| Fw7.17 | - - - G | G R - A G - R | S - - - - - - - - | 210 ± 50 |
| Fw7.18 | - - - - | - R - - - - R | - - - - L - P - - | 310 ± 100 |

B

| | IC$_{50}$ (nM) | | | Ubv binding F-box sequence |
|---|---|---|---|---|
| | Fw7.5 | Fw11.1 | Fw11.2 | |
| Fbw7 | 99 ± 10 | NB | NB | L L P K - - - - E L A L Y V L S |
| Fbw2 | 760 ± 30 | NB | NB | L L P L - - - - E L S F Y L L K |
| Fbl1 | 3300 ± 600 | NB | NB | S L P D - - - - E L L L G I S F |
| Fbw5 | WB | NB | NB | L L P D - - - - S L V Y Q I F L |
| Fbw1 | NB | WB | WB | A L P A R G L D H I A E N I L S |
| Fbw11 | NB | 230 ± 20 | 130 ± 20 | A L P E Q G L D H I A E N I L S |
| Fbw12 | NB | NB | NB | R L P D - - - - L A L K R I F S |

C

| | Region 1 | IC$_{50}$ (nM) |
|---|---|---|
| | 8 9 10 11 a b c d e f g h | Skp1-F-box$^{Fbw11}$ |
| Fw11.1 | Y P Y K S G S Y H N N Y | 360 ± 80 |
| Fw11.2 | - - - - Y - T - - H - - | 108 ± 5 |
| Fw11.3 | - - - - - - T F - - - - | 140 ± 19 |
| Fw11.4 | - - - - Y - - - - - - - | 177 ± 22 |
| Fw11.5 | - - - - - - T - - - - - | 211 ± 40 |
| Fw11.6 | - - - - - - T F - D - - | 1883 ± 50 |

Figure 7

| | \multicolumn{12}{c}{Region 1} | | | | | | | | | | | |
|---|---|---|---|---|---|---|---|---|---|---|---|---|
| | 6 | 9 | 10 | 11 | a | b | c | d | e | f | g | h |
| Library 4 | Y | P | Y | K | S | G | S | Y | H | N | N | Y |
| Fw11.2  | - | - | - | - | Y | - | T | - | - | H | - | - |
| Fw11.3  | - | - | - | - | - | - | T | F | - | - | - | - |
| Fw11.4  | - | - | - | - | Y | - | - | - | - | - | - | - |
| Fw11.5  | - | - | - | - | - | - | T | - | - | - | - | - |
| Fw11.6  | - | - | - | - | - | - | T | F | - | D | - | - |
| Fw11.7  | - | - | - | - | - | - | T | - | - | H | - | - |
| Fw11.8  | - | - | - | - | Y | - | T | - | - | - | - | - |
| Fw11.9  | - | - | - | - | - | - | - | F | - | - | - | - |
| Fw11.10 | - | - | - | - | - | - | - | - | - | H | - | - |
| Fw11.11 | - | - | - | - | - | - | N | F | - | - | - | - |
| Fw11.12 | - | - | - | - | - | - | - | - | - | D | - | - |
| Fw11.13 | - | - | - | - | H | - | - | - | - | Y | - | - |
| Fw11.14 | - | - | - | - | Y | - | - | F | - | - | - | - |
| Fw11.15 | - | - | - | R | - | - | T | - | - | - | - | - |
| Fw11.16 | - | - | - | - | T | - | - | - | - | - | - | - |
| Fw11.17 | - | - | - | - | A | - | - | - | - | - | - | - |

UBIQUITIN VARIANT MODULATORS OF SCF E3 LIGASES AND THEIR USES

FIELD OF THE INVENTION

This invention relates to ubiquitin variants that specifically bind to SCF E3 ligases, and use of these variants to modulate the activity of SCF E3 ligases.

BACKGROUND OF THE INVENTION

The ubiquitin proteasome system (UPS) plays a central role in protein homeostasis through ubiquitination and degradation of substrate proteins. General inhibitors of the proteasome have proven effective in cancer therapy (Weathington, 2014), and thus there is great interest in developing specific inhibitors of UPS enzymes to explore their biological functions and to provide paths to more specific therapeutics. The central player in the UPS is ubiquitin (Ub), a highly conserved 76-residue protein. Ub is covalently attached to protein substrates through sequential action of ubiquitin activating (E1), ubiquitin conjugating (E2), and ubiquitin ligating (E3) enzymes. E3 ligases bind protein substrates and thus dictate specificity of ubiquitination.

E3 ligases constitute the largest class of UPS enzymes, with more than 600 members encoded by the human genome, and are divided into two major classes: a small, well-characterized class of approximately 30 HECT E3 ligases and a much larger, but less-characterized class of hundreds of RING E3 ligases and structurally related variants (Bhowmick). HECT E3 ligases form transient thioester linkages with Ub before transferring it to substrates, while RING ligases serve as adaptors to recruit Ub-charged E2 enzymes to substrates for Ub transfer. The archetype for the RING class is the multi-subunit Skp1-Cul1-F-box (SCF) complex family, which contains 69 members in humans (Jin, 2004). The SCF enzyme complexes are composed of constant Rbx1, Cul1, and Skp1 subunits and a variable F-box protein that binds substrates and dictates specificity (FIG. 1A). Rbx1, the RING protein that recruits the E2 enzyme, binds the scaffold protein Cul1, which in turn binds Skp1, an adaptor for F-box proteins. F-box proteins are variable in domain composition but share a common F-box domain that binds Skp1. F-box proteins are subdivided into three subfamilies based on the structure of their substrate binding domains including WD40, LRR, and other domains, referred to as the Fbw, Fbl, and Fbo subfamilies, respectively (Jin, 2004). Numerous F-box proteins are involved in processes relevant to tumorigenesis, including cell proliferation, cell cycle progression, and apoptosis, suggesting that these proteins may be targets for cancer treatment (Wang, 2014).

SUMMARY OF THE INVENTION

In a first aspect, the invention provides ubiquitin variant (Ubv) polypeptides including one or more amino acid substitution in one or more region of a ubiquitin polypeptide, wherein the region is selected from the group consisting of:

(a) region 1 (amino acids 2-14 of SEQ ID NO:1) wherein the polypeptide comprises the structure:

$X_2$-$X_3$-$X_4$-$X_5$-$X_6$-$X_7$-$X_8$-$X_9$-$X_{10}$-$X_{11}$-$X_{12}$-$X_{13}$-$X_{14}$ wherein $X_2$ is selected from the group consisting of H and Q;
$X_4$ is selected from the group consisting of F and L;
$X_8$ is selected from the group consisting of G and L;
$X_9$ is selected from the group consisting of A, S, and T;
$X_{10}$ is selected from the group consisting of G, R, and V;
$X_{11}$ is selected from the group consisting of K and T;
$X_{12}$ is selected from the group consisting of A, G, N, and T;
$X_{14}$ is selected from the group consisting of I and T;
any X not specified optionally has the amino acid sequence of the corresponding position in SEQ ID NO:1; and the polypeptide optionally comprising 1-4 additional amino acids;

(b) region 2 (amino acids 42-49 of SEQ ID NO:1) wherein the polypeptide comprises the structure:

$X_{42}$-$X_{43}$-$X_{44}$-$X_{45}$-$X_{46}$-$X_{47}$-$X_{48}$-$X_{49}$ wherein $X_{42}$ is selected from the group consisting of I, R, T, and V;
$X_{44}$ is selected from the group consisting of I, L, and V;
$X_{46}$ is selected from the group consisting of A, R, S, and Y;
$X_{47}$ is selected from the group consisting of G, H, K, and R;
$X_{48}$ is selected from the group consisting of K, M, and R;
$X_{49}$ is selected from the group consisting of K, L, P, Q, R, and V; and
any X not specified optionally has the amino acid sequence of the corresponding position in SEQ ID NO:1; and (c) region 3 (amino acids 62-78 of SEQ ID NO:1) wherein the polypeptide comprises the structure:

$X_{62}$-$X_{63}$-$X_{64}$-$X_{65}$-$X_{66}$-$X_{67}$-$X_{68}$-$X_{69}$-$X_{70}$-$X_{71}$-$X_{72}$-$X_{73}$-$X_{74}$-$X_{75}$-$X_{76}$-$X_{77}$-$X_{78}$ wherein $X_{62}$ is selected from the group consisting of E, H, and Q;
$X_{63}$ is selected from the group consisting of K and R;
$X_{66}$ is selected from the group consisting of S and T;
$X_{68}$ is selected from the group consisting of H, Q, and R;
$X_{70}$ is selected from the group consisting of L and V;
$X_{71}$ is selected from the group consisting of L, M, V, W, and Y;
$X_{72}$ is selected from the group consisting of F, I, L, R, and V;
$X_{73}$ is selected from the group consisting of F, L, and V;
$X_{74}$ is selected from the group consisting of G, L, P, R, and S;
$X_{75}$ is selected from F, G, K, R, and S;
$X_{76}$ is selected from the group consisting of A, E, G, L, N, R, and V;
$X_{77}$ is selected from the group consisting of E, G, R, and T, or is absent;
$X_{78}$ is selected from the group consisting of A, G, P, and S, or is absent; and any X not specified in said Ubv polypeptide optionally has the amino acid sequence of the corresponding position in SEQ ID NO:1; or a fragment thereof, wherein the sequence of said Ubv polypeptide does not consist of SEQ ID NO:1.

As noted above, any X not specified can optionally have the amino acid sequence of the corresponding position in SEQ ID NO:1 or, alternatively, the sequence of the corresponding position in any of the specific Ubv's listed herein, if different from that of SEQ ID NO:1.

In some embodiments, the Ubv polypeptide includes a substitution in one or more position selected from the group consisting of $X_8$, $X_{11}$, and $X_{73}$ of the amino acid sequence of SEQ ID NO:1. For example, the Ubv polypeptide may include one or more substitution selected from L8G, K11T, and L73F. Furthermore, the Ubv polypeptide may further including a substitution in position $X_{42}$ and/or $X_{68}$. (e.g., R42I in position $X_{42}$ and/or $X_{68}$) and/or H68R. In another option, the Ubv polypeptide may include one or more of the substitutions noted above (e.g., all of said substitutions) and also an amino acid substitution in one or more position selected from the group consisting of $X_9$, $X_{10}$, $X_{12}$, $X_{46}$, $X_{47}$, $X_{49}$, $X_{62}$, $X_{63}$, $X_{72}$, $X_{76}$, $X_{77}$, and $X_{78}$ (e.g., one or more of T9A, G10R, T12A, A46S, G47R, Q49L, Q62H, K63R, R72I, R76N, G77E, and G78S). In a specific example, the Ubv polypeptide includes each of the substitutions (Fw7.1). In other examples, the Ubv polypeptide includes one or more substitution selected from L8G, K11T, and L73F (e.g., all of said three substitutions) and one of the following sets of substitutions: (a) G10V, T12N, T14I, R42T, Q62E, T66S, H68R, R74G, R76L, 77T, and 78A (Fw7.2); (b) Q2H, F4L, G10V, R42I, I44V, A46Y, H68Q, V70L, R74L, 77R, and 78P (Fw7.3); or (c) T9A, T12N, R42I, A46S, Q49L, Q62H, K63R, H68R, R72I, R76N, 77E, and 78A (Fw7.4).

In another aspect, the invention provides Ubv polypeptide that include one or more amino acid substitution selected from the group consisting of A12G, I42R or V, L49R, H62Q, R63K, and G75R in the amino acid sequence of Fw7.1, wherein amino acids 77 and 78 are optional. In one example, the Ubv polypeptide includes the following substitutions: A10G, I42V, L49R, H62Q, R63K, I72V, R74G, G75R, and G76R (Fw7.5), wherein amino acids 77 and 78 are optional. In other examples, the Ubv polypeptide of claim 10, including the following substitutions: (a) A10G, L49R, H62Q, R63K, R74P, and G75S (Fw7.6); (b) A10G, I42R, S46A, R47G, K48R, L49R, H62Q, R63K, L71Y, I72V, and G75R (Fw7.7); (c) I42R, S46A, R47G, H62Q, R63K, L71W, I72F, F73L, G75F, and G76V (Fw7.8); (d) A10G, L49R, H62Q, R63K, L71M, I72V, R74S, and G75K (Fw7.9); (e) A9T, A10G, I42V, I44L, L49V, H62Q, R63K, L71W, I72L, F73L, and G75R (Fw7.10); (f) E36G, I42V, R47K, L49R, H62Q, R63K, and G75R (Fw7.11); (g) I42R, S46A, R47G, L49R, H62Q, R63K, I72L, G75R, and G76E (Fw7.12); (h) A9S, A10G, E36G, I44L, L49R, H62Q, R63K, R74S, and G76A (Fw7.13); (i) E36D, I42V, I44L, S46R, L49K, H62Q, R63K, V70L, L71W, F73V, and G75R (Fw7.14); (j) A10G, R47H, K48M, L49R, H62Q, R63K, and R74S (Fw.7.15); (k) A10G, E36G, I44L, L49P, H62Q, R63K, L71V, I72V, and G75R (Fw7.16); (l) A10G, E36G, I42R, S46A, R47G, L49R, H62Q, R63K, and T66S (Fw7.17); and (m) I42R, L49R, H62Q, R63K, I72L, and R74P (Fw7.18); wherein amino acids 77 and 78 are optional.

In a third aspect, the invention provides Ubv polypeptides that include the amino acid sequence of Fw11.1 (SEQ ID NO:20), optionally including 1-10, e.g., 1-5, or 1-3 substitutions, which optionally may be in the region of amino acids 1-25, 5-20, 10-19, or 11-17. For example, one of the following sets of substitutions may be included: (a) S12Y, S14T, and N17H (Fw11.2; SEQ ID NO:21); (b) S14T and Y15F (Fw11.3; SEQ ID NO:22); (c) S12Y (Fw11.4; SEQ ID NO:23); (d) S14T (Fw11.5; SEQ ID NO:24); (e) S14T, Y15F, and N17D (Fw11.6; SEQ ID NO:25); (f) S14T and N17H (Fw11.7; SEQ ID NO:26); (g) S12Y and S14T (Fw11.8; SEQ ID NO:27); (h) Y15F (Fw11.9; SEQ ID NO:28); (i) N17H (Fw11.10; SEQ ID NO:29); (j) S14N and Y15F (Fw11.11; SEQ ID NO:30); (k) N17D (Fw11.12; SEQ ID NO:31); (l) S12H and N17Y (Fw11.13; SEQ ID NO:32); (m) S12Y and S15F (Fw11.14; SEQ ID NO:33); (n) K11R and S14T (Fw11.15; SEQ ID NO:34); (o) S12T (Fw11.16; SEQ ID NO:35); and (p) S12A (Fw11.17; SEQ ID NO:36).

In a fourth aspect, the invention provides a Ubv polypeptide including a sequence selected from the group consisting of SEQ ID NOs:2-36, or a variant thereof including a sequence that is at least 90% (e.g., 95%, 97%, or 99%) identical to a sequence selected from the group consisting of SEQ ID NOs:2-36, or a fragment thereof. Optionally, the variant sequence (e.g., a substitution of 1, 2, 3, 4, 5, 6, 7, 8, 9, or 10 amino acids) occurs in the region of amino acids 1-25, 5-20, 10-19, or 11-17.

In a fifth aspect, the invention provides nucleic acid molecules (e.g., isolated nucleic acid molecules) encoding a Ubv polypeptide as described herein, as well as recombinant expression vectors including one or more of such nucleic acid molecule, and host cells including one or more of said nucleic acid molecules or recombinant expression vectors.

In a sixth aspect, the invention provides methods for obtaining ubiquitin variant polypeptides that bind to a Skp1-F-box protein complex. These methods include randomizing sequences in region 1, region 2, and/or region 3 of ubiquitin to create a library of variants, and screening the library of variants for binding to the F-box protein of the Skp1-F-box protein complex, or a fragment thereof, optionally wherein region 1 includes up to 8 amino acids in addition to those present in ubiquitin. In various examples, the F-box protein includes Fbw7 or Fbw11, or a fragment thereof.

In a seventh aspect, the invention provides methods of modulating the activity of an Skp1-Cul1-F-box (SCF) E3 ligase (e.g., and SCF E3 ligase including Fbw7 or Fbw11) in a cell. These methods include contacting the cell with an agent that alters binding of Cul1 to a complex including Skp1 and an F-box protein in the cell. The agent can optionally decrease the activity of the SCFE3 ligase and/or decrease or inhibit binding of Cul1 to the complex including Skp1 and an F-box protein. Furthermore, the agent may optionally include a Ubv polypeptide, a nucleic acid molecule encoding a Ubv polypeptide, or a fragment thereof (e.g., such molecules as described herein). In addition, the agent may have specificity for a particular SCF E3 ligase, or may be active against more than one SCF E3 ligase. In various examples, the cell is a cancer cell, which optionally is within a subject having cancer. Thus, the invention includes methods of treating cancer in a subject, in which the activity of an Skp1-Cul1-F-box (SCF) E3 ligase in a cell of the subject is modulated as described herein.

In an eighth aspect, the invention provides methods of identifying an agent that modulates the activity of an SCF E3 ligase in a cell. These methods include contacting a cell expressing an SCF E3 ligase with a candidate agent (e.g., a small molecule compound), and determining whether the agent affects the binding of Cul1 to a complex including Skp1 and an F-box protein (e.g., by use of an immunoprecipitation assay). In various examples, the cell further expresses a Ubv polypeptide, such as a Ubv polypeptide as described herein.

BRIEF DESCRIPTION OF THE DRAWINGS

FIG. 3. Ubvs selected for binding to the F-box$^{Fbw7}$ or F-box$^{Fbw11}$ domain in complex with full-length Skp1. (A) Ubvs selected from Library 2 for binding to Skp1-F-box$^{Fbw7}$. Positions that were soft randomized in the library are shown and residues conserved as Ubv.Fw7.1 sequence are indicated by dashes. Positions that diverge from the Ubv.Fw7.1 sequence but show consensus amongst the selected sequences are boxed and conserved residues at these positions are shaded grey. (B) Affinities of Ubv.Fw7.5, Ubv.Fw11.1, and Ubv.Fw11.2 for different Skp1-F-box complexes. "NB" indicates no detectable binding and "WB" indicates weak binding for which IC$_{50}$ values were >5000 nM. Sequence of Ubv binding region (F-box residues located within 10 Å of Ubv in the structure of Skp1tr-F-box$^{Fbw7}$-Ubv.Fw7.1 complex) is shown for each F-box protein. Conserved positions are shaded grey and Fbw7 residues important for binding to Ubv.Fw7.1 (FIG. 2F) are boxed. (C) The sequences and affinities of Ubv.Fw11.1 and its derivatives selected for binding to Skp1-F-box$^{Fbw11}$. Only the sequence in Region 1 that differs from Ubv.Fw7.5 is shown, and residues conserved as Ubv.Fw11.1 sequence are indicated by dashes.

FIG. 7. Ubvs selected for binding to the Skp1-F-box$^{Fbw11}$ complex. Only positions in Region 1 that were diversified in the library are shown and residues conserved as Ubv.Fw11.1 sequence are indicated by dashes.

DETAILED DESCRIPTION

Figure 1:
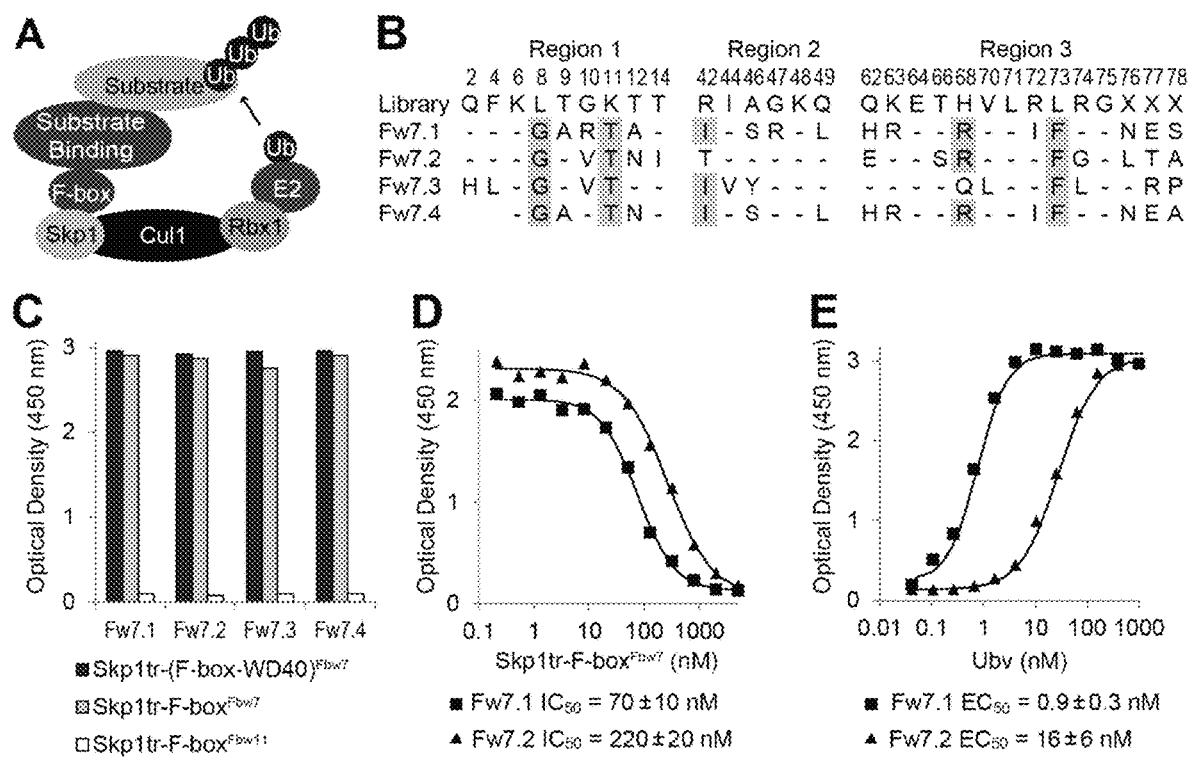
FIG. 1. Ubvs selected for binding to the Skp1tr-Fbw7 complex. (A) Schematic of SCF E3 ligase. (B) Sequence alignment of selected Ubvs. Library 1 sequence is shown, where residue letters indicate the wt Ub sequence that was soft randomized and X denotes positions that were completely randomized. Only diversified positions are shown and residues in Ubvs conserved as wt Ub are indicated by dashes. Sequences showing conservation across selected Ubvs are highlighted in grey. (C) Binding of selected Ubvs to Skp1tr in complex with F-box-WD40$^{Fbw7}$, F-box$^{Fbw7}$, or F-box$^{Fbw11}$. Ubv-phage binding was measured by ELISA with the indicated immobilized proteins. (D and E) Binding of purified Ubv.Fw7.1 or Ubv.Fw7.2 to Skp1tr-F-box$^{Fbw7}$ as measured by ELISA. Data from a typical experiment are shown and the binding values are represented as mean±S.E. of at least two experiments. (D) IC$_{50}$ values were calculated by competitive ELISA as the concentration of Skp1tr-F-box$^{Fbw7}$ in solution that blocked 50% of Ubv binding to immobilized Skp1tr-F-box$^{Fbw7}$. (E) EC$_{50}$ values were calculated by direct-binding ELISA as the concentration of Ubv at which 50% of the saturation signal is achieved for binding to immobilized Skp1tr-F-box$^{Fbw7}$ complex.

The attachment of ubiquitin (Ub) to target proteins involves the activities of Ub-activating enzymes (E1 enzymes), Ub-conjugating enzymes (E2 enzymes), and Ub ligases (E3 enzymes). Ubiquitination can alter the properties of target proteins in many ways, including directing them to the proteasome for degradation, as well as altering their cellular localization, activities, and/or interactive properties with respect to other proteins. Modification of ubiquitination thus provides an opportunity to modify a very wide variety of different cellular functions, in many contexts.

The present invention provides ubiquitin (Ub) variants, or UbVs, which target a particular family of E3 ligases, SCF E3 ligases. The invention also provides nucleic acid molecules encoding such UbVs, as well as related vectors and cells. In addition, the invention provides methods for identifying and characterizing new SCF E3 ligase-specific UbVs. Furthermore, the invention provides methods of using UbV polypeptides and related molecules. Examples of the latter include, for example, methods of identifying other modulators of SCF E3 ligase activity, as well as therapeutic methods involving SCF E3 ligase activity modulation. These and other aspects of the invention are described further, as follows.

The UbVs of the invention bind to or otherwise impact the activity of one or more SCF E3 ligase. The UbVs of the invention can have broad activity, against a wide range of SCF E3 ligases or, alternatively, may be relatively specific, modulating the activity of a small, related subset of SCF E3 ligases or even only a single, specific SCF E3 ligase. The UbVs modulate the activity of an SCF E3 ligase by, for example, blocking or decreasing the ligase activity. The modulation (blocking or decreasing of activity) can be by direct interaction with an SCF E3 ligase. In one example of such an interaction, a UbV binds to an SCF E3 ligase with greater affinity than Ub, resulting in competitive inhibition. In one specific example, the UbV binds to the interface of Skp1 and F-box proteins and thereby prevents Cul1 binding to the same surface and inhibits SCF E3 ligase activity by disrupting complex formation.

SCF E3 ligases that can be targeted by the UbVs of the invention include those containing F-box proteins selected from the Fbw, Fbl, and Fbo families. For example, the SCF E3 ligases can include human Fbw7 or Fbw11 F-box proteins. Additional examples include: Fbw1, Fbw2, Fbw4, Fbw5, Fbw8, Fbw9, Fbw10, Fbw12, Fbl1, Fbl2, Fbl3, Fbl4, Fbl5, Fbl6, Fbl7, Fbl8, Fbl10, Fbl11, Fbl12, Fbl13, Fbl14, Fbl15, Fbl16, Fbl17, Fbl19, Fbl20, Fbl21, Fbl22, Fbo1, Fbo2, Fbo3, Fbo4, Fbo5, Fbo6, Fbo7, Fbo8, Fbo9, Fbo10, Fbo11, Fbo15, Fbo16, Fbo17, Fbo18, Fbo20, Fbo21, Fbo22, Fbo24, Fbo25, Fbo27, Fbo28, Fbo30, Fbo31, Fbo32, Fbo33, Fbo34, Fbo36, Fbo38, Fbo39, Fbo40, Fbo41, Fbo42, Fbo43, Fbo44, Fbo45, Fbo46, Fbo48. Additional SCF E3 ligases that can be targeted include SCF E3 ligases from other eukaryotic species and eukaryotic-like F-box effectors from bacteria.

The UbVs of the invention comprise one or more mutation (e.g., substitution, deletion, addition, or modification) within any region or regions of a wild-type Ub. Using the sequence of human ubiquitin as a reference (SEQ ID NO:1), the UbVs can have mutations (e.g., substitutions, deletions, or insertions) in one or more (e.g., 2, 3, 4, 5, 6, 7, 8, 9, 10, 11, 12, 13, or 14) amino acid in one or more of region 1 (amino acids 2-14), region 2 (42-49), or region 3 (62-78). A wild-type variant having two C-terminal glycines added to the sequence of SEQ ID NO:1 can also serve as a basis for generating UbVs. Furthermore, in addition to human Ub, the invention features UbVs obtained on the basis of Ub from other species and sources.

The sequence of Ub and specific examples of UbVs of the invention are provided in Table 1.

TABLE 1

| SEQ ID NO | Target | Ubv | Ubv sequence |
|---|---|---|---|
| 1 | | Ub | MQIFVKTLTGKTITLEVEPSDTIENVKAKIQDKEGIPPDQQRLIFAGKQLEDGRTLSDYNIQKESTLHLVLRLRGG[GG] |
| 2 | Skp1 (38-43Δ, 70-77Δ, K78G E79S K80G R81G)-Fbw7 | Fw7.1 | MQIFVKTGARTAITLEVEPSDTIENVKAKIQDKEGIPPDQQILIFSRKLLEDGRTLSDYNIHRESTLRLVLIFRGNES |
| 3 | Skp1 (38-43Δ, 70-77Δ, K78G E79S K80G R81G)-Fbw7 | Fw7.2 | MQIFVKTGTVTNIILEVEPSDTIENVKAKIQDKEGIPPDQQTLIFAGKQLEDGRTLSDYNIEKESSLRLVLRFGGLTA |
| 4 | Skp1 (38-43Δ, 70-77Δ, K78G E79S K80G R81G)-Fbw7 | Fw7.3 | MHILVKTGTVTTITLEVEPSDTIENVKAKIQDKEGIPPDQQILVFYGKQLEDGRTLSDYNIQKESTLQLLLRFLGGRP |
| 5 | Skp1 (38-43Δ, 70-77Δ, K78G E79S K80G R81G)-Fbw7 | Fw7.4 | MQIFVKTGAGTNITLEVEPSDTIENVKAKIQDKEGIPPDQQILIFSGKLLEDGRTLSDYNIHRESTLRLVLIFRGNEA |
| 6 | SKp1-Fbw7 | Fw7.5 | MQIFVKTGARTGITLEVEPSDTIENVKAKIQDKEGIPPDQQVLIFSRKRLEDGRTLSDYNIQKESTLRLVLVFGRR |
| 7 | SKp1-Fbw7 | Fw7.6 | MQIFVKTGARTGITLEVEPSDTIENVKAKIQDKEGIPPDQQILIFSRKRLEDGRTLSDYNIQKESTLRLVLIFPSG |
| 8 | SKp1-Fbw7 | Fw7.7 | MQIFVKTGARTGITLEVEPSDTIENVKAKIQDKEGIPPDQQRLIFAGRRLEDGRTLSDYNIQKESTLRLVYVFRRG |
| 9 | SKp1-Fbw7 | Fw7.8 | MQIFVKTGARTAITLEVEPSDTIENVKAKIQDKEGIPPDQQRLIFAGKLLEDGRTLSDYNIQKESTLRLVWFLRFV |
| 10 | SKp1-Fbw7 | Fw7.9 | MQIFVKTGARTGITLEVEPSDTIENVKAKIQDKEGIPPDQQILIFSRKRLEDGRTLSDYNIQKESTLRLVMVFSKG |
| 11 | SKp1-Fbw7 | Fw7.10 | MQIFVKTGTRTGITLEVEPSDTIENVKAKIQDKEGIPPDQQVLLFSRKVLEDGRTLSDYNIQKESTLRLVWLLRRG |
| 12 | SKp1-Fbw7 | Fw7.11 | MQIFVKTGARTAITLEVEPSDTIENVKAKIQDKGGIPPDQQVLIFSKKRLEDGRTLSDYNIQKESTLRLVLIFRRG |
| 13 | SKp1-Fbw7 | Fw7.12 | MQIFVKTGARTAITLEVEPSDTIENVKAKIQDKEGIPPDQQRLIFAGKRLEDGRTLSDYNIQKESTLRLVLLFRRE |
| 14 | SKp1-Fbw7 | Fw7.13 | MQIFVKTGSRTGITLEVEPSDTIENVKAKIQDKGGIPPDQQILLFSRKRLEDGRTLSDYNIQKESTLRLVLIFSGA |
| 15 | SKp1-Fbw7 | Fw7.14 | MQIFVKTGARTAITLEVEPSDTIENVKAKIQDKDGIPPDQQVLLFRRKKLEDGRTLSDYNIQKESTLRLLWIVRRG |
| 16 | SKp1-Fbw7 | Fw7.15 | MQIFVKTGARTGITLEVEPSDTIENVKAKIQDKEGIPPDQQILIFSHMRLEDGRTLSDYNIQKESTLRLVLIFSGG |
| 17 | SKp1-Fbw7 | Fw7.16 | MQIFVKTGARTGITLEVEPSDTIENVKAKIQDKGGIPPDQQILLFSRKPLEDGRTLSDYNIQKESTLRLVVVFRRG |
| 18 | SKp1-Fbw7 | Fw7.17 | MQIFVKTGARTGITLEVEPSDTIENVKAKIQDKGGIPPDQQRLIFAGKRLEDGRTLSDYNIQKESSLRLVLIFRGG |
| 19 | SKp1-Fbw7 | Fw7.18 | MQIFVKTGARTAITLEVEPSDTIENVKAKIQDKEGIPPDQQRLIFSRKRLEDGRTLSDYNIQKESTLRLVLLFPGG |
| 20 | Skp1-Fbw11 | Fw11.1 | MQIFVKTYPYKSGSYHNNYTITLEVEPSDTIENVKAKIQDKEGIPPDQQVLIFSRKRLEDGRTLSDYNIQKESTLRLVLVFGRR |
| 21 | Skp1-Fbw11 | Fw11.2 | MQIFVKTYPYKGTYHNNYTITLEVEPSDTIENVKAKIQDKEGIPPDQQVLIFSRKRLEDGRTLSDYNIQKESTLRLVLVFGRR |
| 22 | Skp1-Fbw11 | Fw11.3 | MQIFVKTYPYKSGTFHNNYTITLEVEPSDTIENVKAKIQDKEGIPPDQQVLIFSRKRLEDGRTLSDYNIQKESTLRLVLVFGRR |
| 23 | Skp1-Fbw11 | Fw11.4 | MQIFVKTYPYKGSYHNNYTITLEVEPSDTIENVKAKIQDKEGIPPDQQVLIFSRKRLEDGRTLSDYNIQKESTLRLVLVFGRR |

TABLE 1-continued

| SEQ ID NO | Target | Ubv | Ubv sequence |
|---|---|---|---|
| 24 | Skp1-Fbw11 | Fw11.5 | MQIFVKTYPYKSGTYHNNYTITLEVEPSDTIENVKAKIQDK EGIPPDQQVLIFSRKRLEDGRTLSDYNIQKESTLRLVLVFG RR |
| 25 | Skp1-Fbw11 | Fw11.6 | MQIFVKTYPYKSGTFHDNYTITLEVEPSDTIENVKAKIQDK EGIPPDQQVLIFSRKRLEDGRTLSDYNIQKESTLRLVLVFG RR |
| 26 | Skp1-Fbw11 | Fw11.7 | MQIFVKTYPYKSGTYHHNYTITLEVEPSDTIENVKAKIQDK EGIPPDQQVLIFSRKRLEDGRTLSDYNIQKESTLRLVLVFG RR |
| 27 | Skp1-Fbw11 | Fw11.8 | MQIFVKTYPYKYGTYHNNYTITLEVEPSDTIENVKAKIQDK EGIPPDQQVLIFSRKRLEDGRTLSDYNIQKESTLRLVLVFG RR |
| 28 | Skp1-Fbw11 | Fw11.9 | MQIFVKTYPYKSGSFHNNYTITLEVEPSDTIENVKAKIQDK EGIPPDQQVLIFSRKRLEDGRTLSDYNIQKESTLRLVLVFG RR |
| 29 | Skp1-Fbw11 | Fw11.10 | MQIFVKTYPYKSGSYHNNYTITLEVEPSDTIENVKAKIQDK EGIPPDQQVLIFSRKRLEDGRTLSDYNIQKESTLRLVLVFG RR |
| 30 | Skp1-Fbw11 | Fw11.11 | MQIFVKTYPYKSGNFHNNYTITLEVEPSDTIENVKAKIQDK EGIPPDQQVLIFSRKRLEDGRTLSDYNIQKESTLRLVLVFG RR |
| 31 | Skp1-Fbw11 | Fw11.12 | MQIFVKTYPYKSGSYHDNYTITLEVEPSDTIENVKAKIQDK EGIPPDQQVLIFSRKRLEDGRTLSDYNIQKESTLRLVLVFG RR |
| 32 | Skp1-Fbw11 | Fw11.13 | MQIFVKTYPYKHGSYHYNYTITLEVEPSDTIENVKAKIQDK EGIPPDQQVLIFSRKRLEDGRTLSDYNIQKESTLRLVLVFG RR |
| 33 | Skp1-Fbw11 | Fw11.14 | MQIFVKTYPYKYGSFHNNYTITLEVEPSDTIENVKAKIQDK EGIPPDQQVLIFSRKRLEDGRTLSDYNIQKESTLRLVLVFG RR |
| 34 | Skp1-Fbw11 | Fw11.15 | MQIFVKTYPYRSGTYHNNYTITLEVEPSDTIENVKAKIQDK EGIPPDQQVLIFSRKRLEDGRTLSDYNIQKESTLRLVLVFG RR |
| 35 | Skp1-Fbw11 | Fw11.16 | MQIFVKTYPYKTGSYHNNYTITLEVEPSDTIENVKAKIQDK EGIPPDQQVLIFSRKRLEDGRTLSDYNIQKESTLRLVLVFG RR |
| 36 | Skp1-Fbw11 | Fw11.17 | MQIFVKTYPYKAGSYHNNYTITLEVEPSDTIENVKAKIQDK EGIPPDQQVLIFSRKRLEDGRTLSDYNIQKESTLRLVLVFG RR |

In addition to UbVs having the sequences set forth above, the invention includes variants of these and other UbVs. Thus, for example, the invention includes polypeptides having at least 80%, 85%, 95%, or 99% sequence identity to a UbV, such as a UbV described herein. The invention also includes UbV variants having one or more (e.g., 2, 3, 4, 5, 6, 7, 8, 9, 10, or more) substitutions (e.g., conservative amino acid substitutions) and/or deletions relative to a sequence provided herein.

A "conservative" amino acid substitution as used herein, is one in which one amino acid residue is replaced with another amino acid residue having similar properties. Conservative substitutions typically include substitutions within the following groups: glycine and alanine; valine, isoleucine, and leucine; aspartic acid, glutamic acid, asparagine, and glutamine; serine and threonine; lysine and arginine; and phenylalanine and tyrosine. In more detail, conserved amino acid substitutions involve replacing one or more amino acids of the polypeptides of the invention with one or more amino acids of similar charge, size, and/or hydrophobicity characteristics. When only conserved substitutions are made, the resulting molecule may be functionally equivalent or similar to the original molecule. Changes that result in production of a chemically equivalent or chemically similar amino acid sequence are included within the scope of the invention. In various examples, a hydrophobic residue, such as glycine, can be substituted for another hydrophobic residue such as alanine. An alanine residue may be substituted with a more hydrophobic residue such as leucine, valine, or isoleucine. A negatively charged amino acid, such as aspartic acid, may be substituted for glutamic acid. A positively charged amino acid such as lysine may be substituted for another positively charged amino acid, such as arginine. The phrase "conservative substitution" also includes the use of a chemically derivatized residue in place of a non-derivatized residue, provided that such polypeptide displays a requisite activity.

The invention includes polypeptides that comprise the sequences of the UbVs described herein, in addition to other sequences. Thus, for example, the invention includes fusion proteins comprising the UbVs (and variants thereof) described herein (e.g., fusions with GST, His, Flag, or Myc tags). In addition, the invention includes fragments of the UbVs (and variants thereof) described herein. Such fragments include, for example, a UbV (or variant thereof) having 1-30 (e.g., 2-25, 4-30, or 5-10) amino acids deleted from either or both ends of the UbV (or variant thereof). Internal deletions are also included in the invention. The fragments can optionally be comprised within a fusion protein, as described above in connection with full-length UbVs. Optionally, UbV variants and fragments maintain, at least in part, one or more activities of the UbV from which they are derived. The fragments can further optionally comprise one or more region of a UbV, as described herein (e.g., region 1, region 2, region 3, region 1 and 2, region 2 and 3, etc.)

The UbVs of the invention can be used to obtain or design peptide mimetics, which are also included in the invention. Peptide mimetics include synthetic structures that may serve as substitutes for peptides in interactions between molecules, and include synthetic structures which can optionally contain amino acids and/or peptide bonds, but are designed to retain the desired structural and functional features and thus may be suitable substitutes of the peptide inhibitor analog disclosed herein. Peptide mimetics also include molecules incorporating peptides into larger molecules with other functional elements (e.g., as described in WO 99/25044). Peptide mimetics also include peptoids, oligopeptoids (Simon et al (1972) Proc. Natl. Acad. Sci. USA 89:9367), and peptide libraries containing peptides of a designed length representing all possible sequences of amino acids corresponding to an isolated peptide of the disclosure. Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The UbVs described herein can be made using standard methods including, for example, recombinant methods. The UbVs may also be prepared by chemical synthesis using techniques well known in the art such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)). The UbVs of the invention typically comprise naturally occurring amino acids. However, UbVs including one or more non-naturally occurring amino acid are also included in the invention.

In addition to the UbVs described above, the invention provides nucleic acid molecules encoding the UbVs (e.g., nucleic acid molecules encoding UbVs of any one of SEQ ID NOs:2-36) and variants thereof, as described herein.

The term "nucleic acid molecule" as used herein refers to a sequence of nucleotide or nucleoside monomers consisting of naturally occurring bases, sugars, and intersugar (backbone) linkages. The term also includes modified or substituted sequences comprising non-naturally occurring monomers or portions thereof, which function similarly. The nucleic acid molecules of the present invention can be ribonucleic (RNA) or deoxyribonucleic acids (DNA), and can contain naturally occurring bases including adenine, guanine, cytosine, thymidine, and uracil. The sequences can also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil, and 5-trifluoro cytosine.

The term "isolated and purified" as used herein refers to a nucleic acid molecule, polypeptide, or peptide that is substantially free of cellular material or culture medium when produced by recombinant DNA techniques, or chemical precursors, or other chemicals when chemically synthesized. An "isolated and purified" nucleic acid molecule is also substantially free of sequences which naturally flank the nucleic acid (i.e., sequences located at the 5' and 3' ends of the nucleic acid) from which the nucleic acid molecule is derived.

Nucleic acid molecules encoding the UbVs can optionally be comprised within a vector, such as an expression vector. Exemplary vector types include cosmids, plasmids, or modified viruses (e.g. replication defective retroviruses, adenoviruses, and adeno-associated viruses). The expression vectors can include a nucleic acid molecule encoding a UbV, as well as operatively linked regulatory sequences that are selected based on the type of host cells in which expression is to occur. "Operatively linked" is intended to mean that the nucleic acid molecule is linked to regulatory sequences in a manner that allows expression of the nucleic acid under the control of the regulatory element.

The invention thus includes recombinant expression vectors comprising a nucleic acid molecule encoding a UbV, as described herein, and optionally regulatory sequences that direct transcription of the nucleic acid molecule. Suitable regulatory sequences are known in the art and can be obtained from a variety of sources, including bacterial, fungal, viral, mammalian, and insect genes. Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. Furthermore, the recombinant expression vectors may also contain a selectable marker gene which facilitates the selection of host cells transformed or transfected with a recombinant molecule of the disclosure. Examples of selectable marker genes are genes encoding a protein such as G418 and hygromycin, which confer resistance to certain drugs, β-galactosidase, chloramphenicol acetyltransferase, firefly luciferase, or an immunoglobulin or portion thereof such as the Fc portion of an immunoglobulin optionally IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors. It will be appreciated that selectable markers can be introduced on a separate vector from the nucleic acid of interest.

The recombinant expression vectors can also contain genes that encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.), and pRIT5 (Pharmacia, Piscataway, N.J.), which fuse glutathione S-transferase (GST), maltose E binding protein, or protein A, respectively, to the recombinant protein.

Recombinant expression vectors can be introduced into host cells to produce transformed host cells, which are also included in the invention. Suitable host cells include a wide variety of eukaryotic host cells and prokaryotic cells. For example, the UbVs of the invention can be expressed in mammalian, insect, yeast, or bacterial cells (e.g., *E. coli*).

The nucleic acid molecules of the invention may also be chemically synthesized using standard techniques. Various methods of chemically synthesizing nucleic acid molecules are known, including solid-phase synthesis which, like peptide synthesis, has been fully automated in commercially available DNA synthesizers (see, e.g., Itakura et al., U.S. Pat. No. 4,598,049; Caruthers et al., U.S. Pat. No. 4,458,066; and Itakura, U.S. Pat. Nos. 4,401,796 and 4,373,071).

As noted above, the invention provides methods of identifying and characterized SCF E3 ligase-specific UbVs. Such UbVs can be obtained by screening libraries of Ub variants, which can be generated by randomizing the entire sequence of ubiquitin (SEQ ID NO:1) or particular regions (e.g., one or more of regions 1 (2-14), 2 (42-49), and 3 (62-78), which optionally may be truncated or expanded by, e.g., 1-10 or 2-5 amino acids). Randomization can be achieved using standard methods of genetic engineering. For example, variants can be created in which a particular residue is replaced with a different amino acid, such that a library of variants comprising all 20 amino acids in each position (e.g., within one or more of regions 1, 2, and 3) is produced. In one example, randomization is performed to yield 75% wild type amino acid residues and 25% mutated amino acid residues within, e.g., one or more of regions 1, 2, and 3.

UbV libraries (e.g., phage display libraries) can be screened against one or more SCF E3 ligase (e.g., see the list set forth above) and/or a portion of one or more SCF E3 ligase. In one example, the libraries are screened against a complex including an F-box protein and Skp1, or fragments thereof. In one example, the F-box component of the complex includes only an F-box domain and a substrate binding domain (e.g., a WD40 or LRR domain), while the Skp1 protein is full length or optionally includes truncations in one or more loops (e.g., loop 1 and/or loop 2; see below for example of Skp1tr). UbVs identified as binding to an SCF E3 ligase (or portion or fragment thereof) can then be subject to further characterization including, for example, assessment of binding affinity by $EC_{50}$ determination, specificity for particular SCF E3 ligases (or subgroups thereof), structural features (e.g., by co-crystallization analysis), and effects on ubiquitination. The latter effects of UbVs can be assessed using in vitro ubiquitination assays, as well as in cell-based assays that assess the effects of a UbV on downstream effects of ubiquitination involving a particular SCF E3 ligase. Details of exemplary assays that can be used in this aspect of the invention are provided in the Examples, below.

In addition to being identified and characterized in various assays, as described above, UbVs identified in the screening of libraries can be subject to further mutagenesis, in order to identify additional UbVs having desirable features. Thus, for example, UbVs found to have a desirable property (e.g., binding specificity), but lacking another features (e.g., binding affinity) can be further mutagenized and re-screened, optionally with the sequences of residues surmised by sequence analysis to be important with respect to the already obtained desirable property (e.g., binding specificity) maintained.

The invention also provides methods for modulating SCF E3 ligase activity. These methods include in vivo modulation of SCF E3 ligase activity by administration of a UbV as described herein, or a nucleic acid molecule encoding such a UbV (e.g., a nucleic acid molecule in an expression or delivery vector, such as a vector as described herein) to a subject (e.g., a human patient). Ex vivo methods, in which a UbV polypeptide or nucleic acid molecule is contacted with a cell or tissue that is then introduced into a subject for therapeutic purposes, are also included in the invention.

The therapeutic methods of the invention can be used in the prevention or treatment of diseases and conditions including, for example, cancer. Examples of cancer types that can be treated according to the methods of the invention include brain cancer, ovarian cancer, leukemia, lung cancer, colon cancer, CNS cancer, melanoma, myeloma, renal cancer, prostate cancer, pancreatic cancer, and breast cancer. Additional diseases or conditions that can be treated include sleep and metabolic disorders, immune disorders, Hepatitis C virus-related conditions, and muscle atrophy.

The invention also includes methods of identifying additional agents that can be used to modulate SCF E3 ligase activity, and thus which can be used in the therapeutic methods described above. In such methods, a complex comprising a UbV and an SCF E3 ligase (or a fragment or portion thereof, such as a complex of an F-box protein and Skp1 (or portions thereof; see, e.g., above) is contacted with a candidate agent to determine whether the candidate agent impacts the ability of the UbV to bind to the SCF E3 ligase (or fragment thereof). An agent that affects the binding (e.g., decreases or increases the binding) can be considered as a candidate for modulation of SCF E3 ligase activity and, thus, may be considered for use in a therapeutic method (e.g., see above). Such candidate agents can be tested in an in vitro ubiquitination assay or in cell-based assays, such as those described herein. Candidate agents that can be screened in such assays include, e.g., peptides, nucleic acid molecules, natural products, and small organic or inorganic molecules. Such agents may be present in the context of a library, which can be tested in a high throughput manner.

The following non-limiting examples are illustrative of the present disclosure:

EXPERIMENTAL EXAMPLES

Selection of Ubv Binders for the Skp1tr-Fbw7 Complex

To investigate the potential of using Ubvs to target F-box family members, we used a naïve phage-displayed Ubv library (Ernst) (FIGS. 1B and 5) to perform binding selections against Fbw7 in complex with Skp1. To facilitate structural characterization, we used Fbw7 and Skp1 constructs that were previously used for structural studies but still contained all necessary functional elements required for E3 ligase activity. This included Fbw7 composed of F-box and WD40 domains (F-box-WD40$^{Fbw7}$) (Hao, 2007) and Skp1 with truncations in two loops (Skp1tr) (Schulman, 2000) (Table 2).

The selections yielded four unique binding Ubvs that shared common mutations at several positions (FIG. 1B), suggesting that they all likely bind to a common site on the Skp1tr-Fbw7 complex. To determine the region targeted by the selected Ubvs, we performed phage enzyme-linked immunosorbent assays (ELISAs) against Skp1tr complexed with F-box-WD40$^{Fbw7}$, Fbw7 F-box domain (F-box$^{Fbw7}$) or Fbw11 F-box domain (F-box$^{Fbw11}$). Surprisingly, the Ubvs did not target the WD40 domain, which is known to interact with Ub (Pashkova, 2010) and small molecule inhibitors (Orlicky), but rather, specifically targeted F-box$^{Fbw7}$ in complex with Skp1tr (FIG. 1C). Relative affinities of Ubv.Fw7.1 and Ubv.Fw7.2 were measured for purified proteins with ELISAs that determined half-maximum effective concentration of Ubv binding to immobilized Skp1tr-F-box$^{Fbw7}$ ($EC_{50}$) and half-maximum inhibitory concentration of Skp1tr-F-box$^{Fbw7}$ in solution that inhibited binding of Ubv to immobilized Skp1tr-F-box$^{Fbw7}$ ($IC_{50}$). Since the $IC_{50}$ value reflects the interaction between the two proteins in solution, it provides a good estimate of the affinity (Lee, 2004). Ubv.Fw7.1 exhibited the highest binding activity in both assay formats ($IC_{50}$=70 nM and $EC_{50}$=0.9 nM) and was chosen for further characterization (FIGS. 1D and E).

Structure of Ubv.Fw7.1 in Complex with Skp1tr-F-box$^{Fbw7}$

Figure 2:
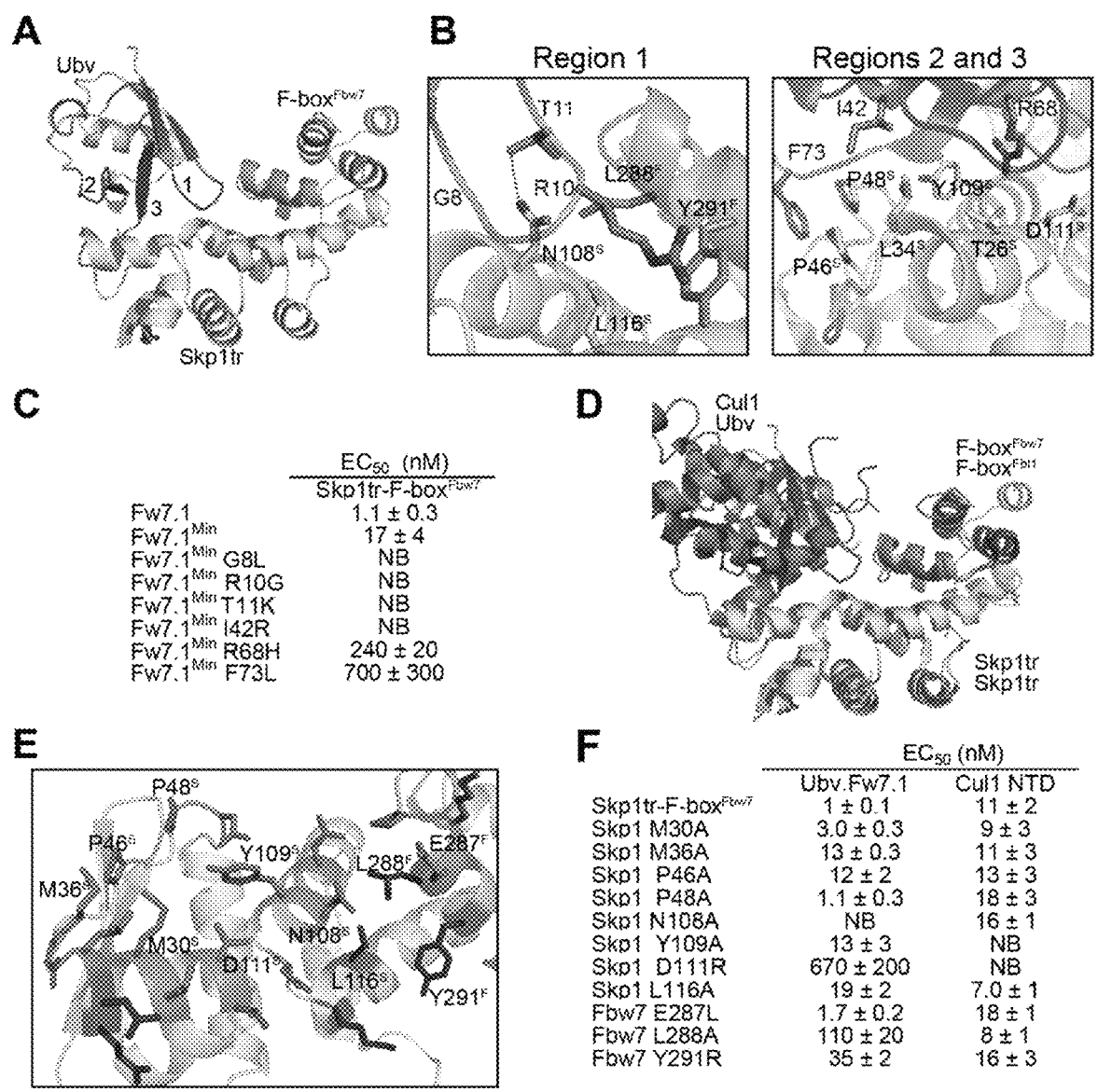
FIG. 2. Structural and mutational analysis of the interactions between Ubv.Fw7.1 and the Skp1tr-F-box$^{Fbw7}$ complex. (A) Structure of Ubv.Fw7.1 in complex with Skp1tr-F-box$^{Fbw7}$. Ubv regions (Regions 1-3) that were diversified in Library 1 are labeled. (B) Details of the molecular interactions between Ubv.Fw7.1 and Skp1tr-F-box$^{Fbw7}$ showing residues that are mutated relative to wt Ub and are critical for binding. Skp1tr and Fbw7 residues are denoted by "S" and "F" superscripts, respectively. (C) Affinities of Ubv.Fw7.1 back-mutants for Skp1tr-F-box$^{Fbw7}$. Ubv.Fw7.1$^{Min}$ lacks Ub tail (residues 75-78) and contains only six mutations relative to wt Ub (L8G, G10R, K11T, R42I, H68R, and L73F). "NB" indicates no detectable binding. (D) Superposition of Skp1tr-F-box$^{Fbw7}$-Ubv.Fw7.1 complex with Skp1tr-F-box$^{Fbl1}$Cul1 complex (PDB: 1LDK). (E) Comparison of the Ubv.Fw7.1-binding and predicted Cul1-binding surfaces on Skp1tr-F-box$^{Fbw7}$. Skp1tr-F-box$^{Fbw7}$ residues interacting with Ubv.Fw7.1 or predicted to interact with Cul1 (by comparison to the Skp1-F-box$^{Fbl1}$-Cul1 complex) are shown as stick and shaded according to predicted interactions: medium grey interacts with Cul1 and Ubv.Fw7.1; light grey, interacts with Cul1 only; dark grey, interacts with Ubv.Fw7.1 only. Residues that were subjected to mutagenesis are labeled. (F) Effects of substitutions in Skp1tr or the F-box$^{Fbw7}$domain on the binding of Skp1tr-F-box$^{Fbw7}$ to Ubv.Fw7.1 or Cul1 N-terminal domain (NTD).
Figure 8:
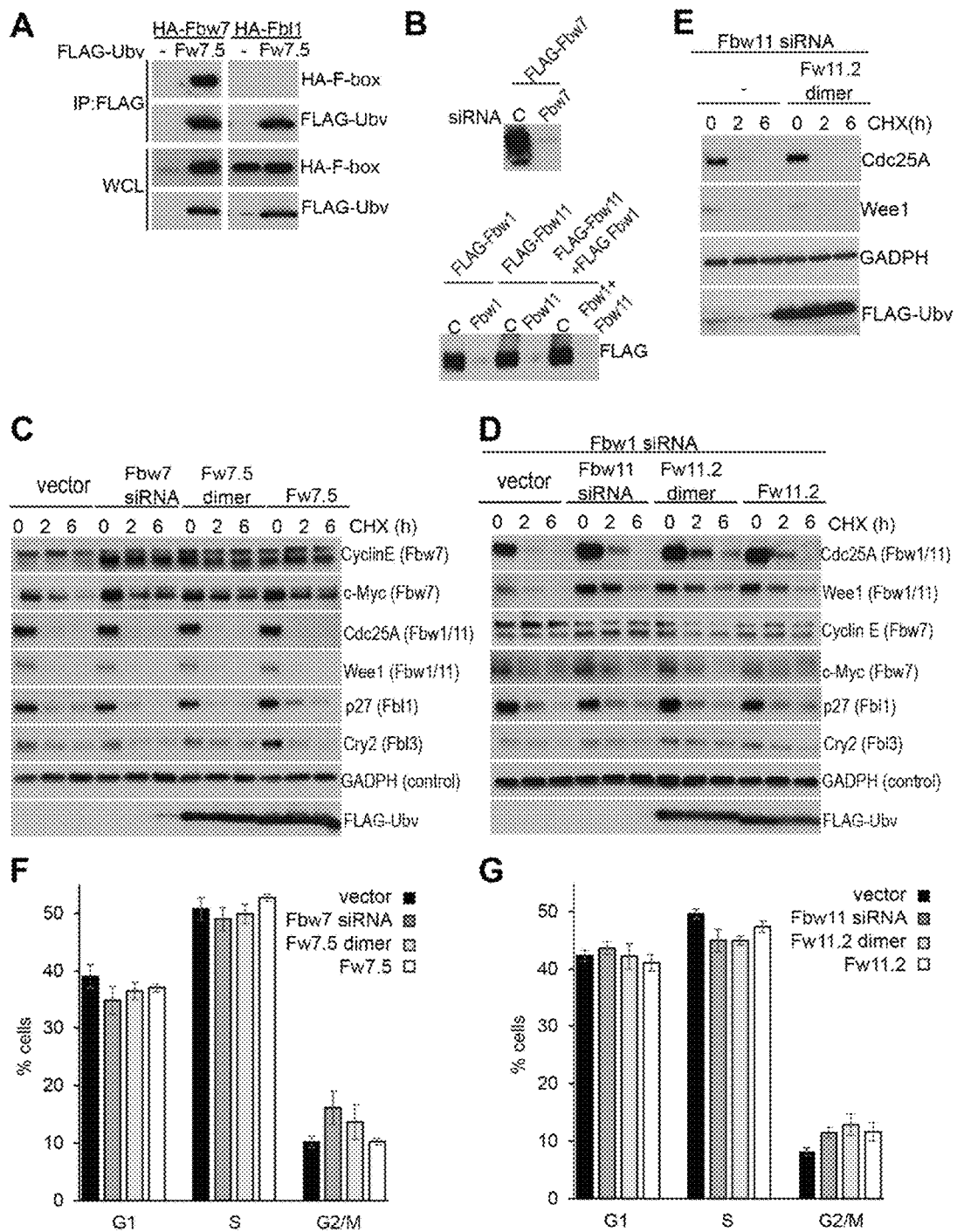
FIG. 8. Additional intracellular experiments. (A) Interaction between FLAG-Ubv.Fw7.5 and exogenously expressed HA-Fbw7 or HA-Fbl1 in cell lysates. FLAG immunoprecipitates were separated on gel electrophoresis and probed for the presence of the indicated HA-tagged F-box proteins. Ubv.Fw7.5 co-immunoprecipitates significant levels of Fbw7, whereas Fbl1 presence in immunoprecipitates could not be detected by this assay. It should be noted that the levels of Fbw7-HA in cell lysates are significantly greater in the presence of Ubv.Fw7.5 expression; this is the result of inhibition of Fbw7 auto-ubiquitination (Welcker, 2013) by the Ubv.Fw7.5. (B) Validation of Fbw7, Fbw1, and Fbw11 siRNA. Cells expressing FLAG-Fbw7 (top panel) and FLAG-Fbw1, FLAG-Fbw11 and FLAG-Fbw1+HA-Fbw11 (bottom panel) were treated either with control siRNA (C) or the siRNAs directed against the indicated proteins. (C) and (D). Expression of Ubv.Fw7.5 (C) and Ubv.Fw11.2 (D) dimer or monomer selectively stabilizes substrates of SCF$^{Fbw7}$ and SCF$^{Fbw11}$ respectively, but not other SCF ligases. Cells were transiently transfected with either siRNA molecules (positive control), empty vector (vector), or vectors expressing FLAG-Ubv. Cells were treated with Cycloheximide (CHX) for the indicated time points and cell lysates were probed with endogeneous antibodies against the indicated proteins (substrate (F-box protein)). (E) Expression of Ubv.Fw11.2 does not affect stability of Cdc25A and Wee1 in the background of Fbw11 siRNA treatment. (F) and (G) Distribution of G1-phase, G2-phase, and S-phase populations in cells expressing Ubv.Fw7.5 (F) and Ubv.Fw11.2 (G). Cells were transiently transfected with either siRNA molecules (positive control), empty vector (vector), or vectors expressing FLAG-Ubv. Analysis of cell cycle kinetics was determined by Hoechst dye (nucleic acid stain) staining, followed by flow cytometry analysis. The graph combines data from three biological replicates and mean±S.E. is shown. (G) The effect of Fbw11 siRNA treatment and Ubv.Fw11.2 expression was assessed in the background of Fbw1 siRNA treatment.

We crystallized Ubv.Fw7.1 in complex with Skp1tr-F-box$^{Fbw7}$ and solved the structure at 2.5 Å resolution by molecular replacement (FIGS. 2A and 8 and see Table 3 for X-ray data collection and refinement statistics). Ubv.Fw7.1 makes extensive contacts with Skp1tr but also makes significant contacts with F-box$^{Fbw7}$ (719 or 144 Å$^2$ of Ubv accessible surface area buried, respectively). The structure of Skp1tr-F-box$^{Fbw7}$ in the ternary complex aligns closely with the previously determined structure of the Skp1tr-(F-box-WD40)$^{Fbw7}$ complex (Hao, 2007), suggesting that Ubv.Fw7.1 does not induce major conformational changes upon binding (RMSD of Skp1=0.93 Å and RMSD of Fbw7 (residues 279-313)=1.07 Å).

Although Ubv.Fw7.1 contains 15 substitutions relative to wild-type (wt) Ub and two additional C-terminal residues, back mutation analysis revealed that only six substitutions (L8G, G10R, K11T, R42I, H68R and L73F) are responsible for most of the enhancement in binding to Skp1tr-Fbw7. A variant containing these six substitutions (Ubv.Fw7.1$^{Min}$) bound to Skp1tr-F-box$^{Fbw7}$ only ~20-fold weaker than Ubv.Fw7.1, but further back mutation of any of the six substitutions greatly reduced or completely abrogated binding (FIG. 2C). Three of the six substitutions (L8G, G10R, and K11T) are located in Region 1, a loop that contacts the Skp1-Fbw7 interface. The Arg-10 side-chain of the Ubv forms cation-pi interaction with the side-chain of Tyr-291$^{Fbw7}$ and its aliphatic portion packs against the side-chains of Leu-288$^{Fbw7}$ and Leu-116$^{Skp1}$. Gly-8 and Thr-11 pack against Asn-108$^{Skp1}$ and the side-chain NH$_2$ of Asn-108$^{Skp1}$ forms a hydrogen bond with the side-chain OH of Thr-11 (FIG. 2B). The other three substitutions (R42I, H68R, and L73F) contact Skp1 only. The Ile-42 side-chain engages in hydrophobic interactions with the side-chain of Leu-34$^{Skp1}$ and the Phe-73 side-chain packs against Pro-46$^{Skp1}$ and Pro-48$^{Skp1}$. The Arg-68 side-chain forms cation-pi interaction with the side-chain of Tyr-109$^{Skp1}$ and polar contacts with the side-chains of Thr-26$^{Skp1}$ and Asp-111$^{Skp1}$ (FIG. 2B).

Notably, the surface on Skp1tr-F-box$^{Fbw7}$ for binding to Ubv.Fw7.1 largely overlaps with the previously elucidated surface on the analogous Skp1-F-box$^{Fbl1}$ complex for binding to Cul1 (Zheng, 2002) (FIGS. 2D and E). To compare the energetics of Ubv.Fw7.1 and Cul1 binding to Skp1tr-F-box$^{Fbw7}$, we constructed a series of point mutants at positions within the common interface and measured the effects on binding to both ligands (FIG. 2F). Three of the substitutions (N108A$^{Skp1}$, Y109A$^{Skp1}$ and D111R$^{Skp1}$), which reside in the center of binding surface, either abolished or significantly disrupted binding to both Ubv.Fw7.1 and Cul1 and most of the other substitutions also had significant effects on binding to both ligands. These results show that Ubv.Fw7.1 and Cul1 share a common structural and functional binding site on the Skp1tr-F-box$^{Fbw7}$ complex.

Figure 6:
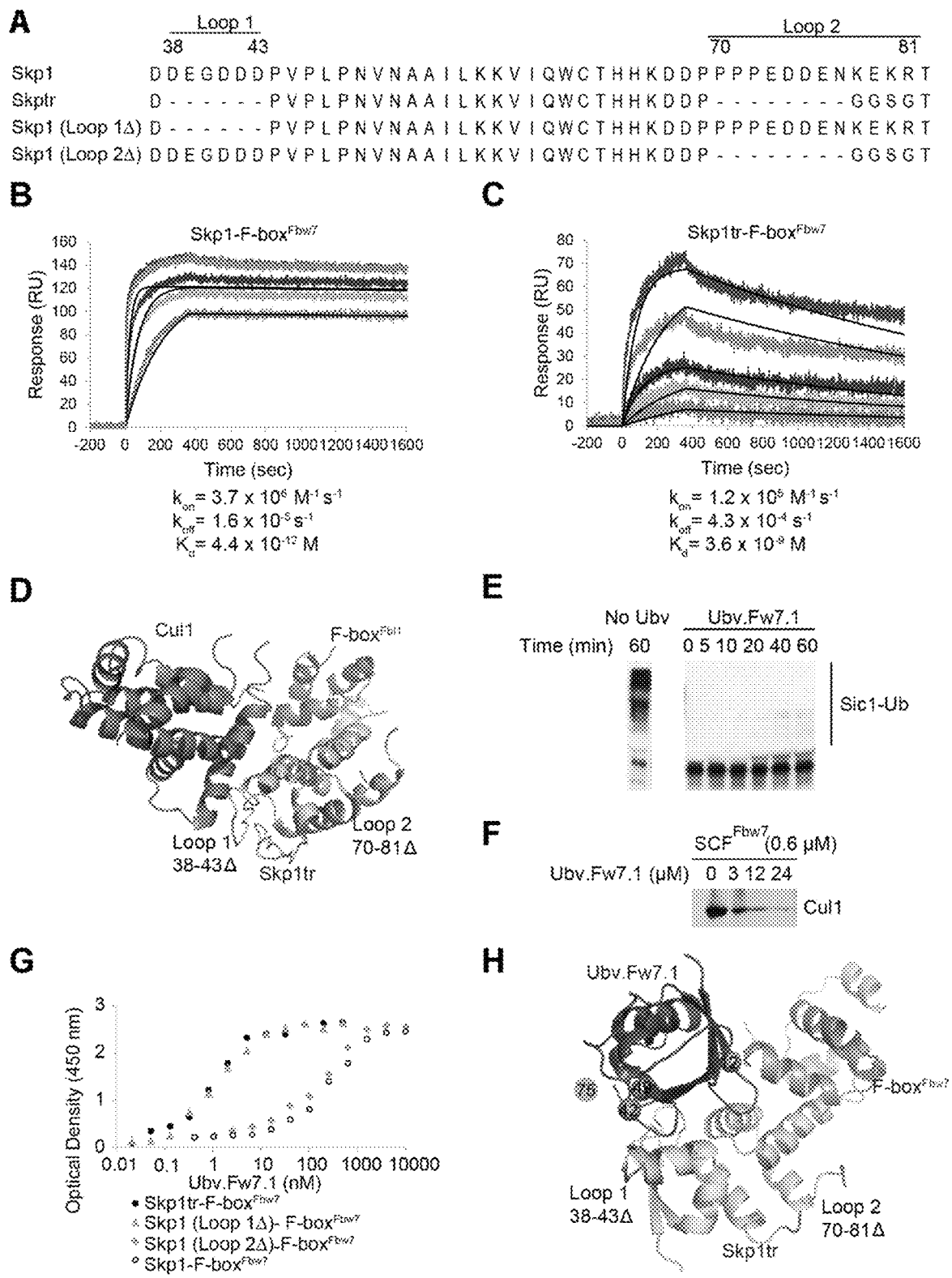
FIG. 6. Additional in vitro experiments (A) Alignment of all Skp1 constructs tested in this study. Loop 1 (residues 38-43) and Loop 2 (residues 70-81) indicate residues deleted in truncated version of Skp1 (Skp1tr). (B) and (C) Binding of Cul1 N-terminal domain (NTD) to Skp1-F-box$^{Fbw7}$ and Skp1tr-F-box$^{Fbw7}$ complexes demonstrates importance of Skp1 Loop 1 and Loop 2 residues for interaction with Cul1. Binding was measured by Surface Plasmon Resonance (SPR) analysis and obtained traces are shown for Cul1 NTD interaction with Skp1-F-box$^{Fbw7}$ (B) and Skp1tr-F-box$^{Fbw7}$ (C). Skp1-F-box complexes were immobilized and Cul1 NTD was injected at different concentrations (100, 33, 11, 3.7 and 1.2 nM). Black lines represent fits to a simple 1:1 Langmuir binding isotherm model. In the case of binding to Skp1-F-box$^{Fbw7}$ only 3 lowest Cul1 concentrations (11 nM Cul1, 3.7 nM Cul1, and 1.2 nM Cul1) were used to fit the data, since higher concentrations exceeded estimated affinity of the interaction >1000 fold. Estimated $k_{on}$, $k_{off}$ rates and Kd of the interactions are indicated. (D) Structure of Skp1tr-F-box$^{Fbl1}$-Cul1 (PDB: 1LDK) complex highlighting positions of loops deleted in Skp1tr in relation to Cul1 binding surface. Location of loops deleted in Skp1tr are indicated. (E) Ubv.Fw7.1 promotes dissociation of Cul1 from the SCF$^{Fbw7}$complex. SCF$^{Fbw7}$ complex containing GST-tagged Skp1tr on glutathionine sepharose resin was incubated for 1 hour with increasing amounts of Ubv.Fw7.1. Cul1 remaining bound to the resin was detected by western blot. (F) Ubv.Fw7.1 blocks ubiquitination activity of SCF$^{Fbw7}$. A functional SCF$^{Fbw7}$ complex was assembled from the Skp1tr-(F-box-WD40)$^{Fbw7}$ and Cul1-Rbx1 complexes purified separately. Sic1, which is a natural substrate of yeast Fbw7 but is also recognized by human Fbw7, was used as the substrate. The ubiquitination reaction containing E1 (0.5 µM), E2 (14 µM), and SCF$^{Fbw7}$ (0.4 µM) was initiated by adding Ub (25 µM) to purified components in the absence and presence of Ubv.Fw7. 1 (25 µM). The products of Sic1 (0.4 µM) ubiquitination were visualized by western blotting at the indicated time points. (G) Skp1 Loop 1 (residues 38-43) interferes with binding to Ubv.Fw7.1, while Skp1 Loop 2 (residues 70-81) has no effect on binding. Binding was tested by protein ELISA and dose response curves of Ubv.Fw7.1 binding to different Skp1 constructs in complex with F-box$^{Fbw7}$ domain are shown. (H) Structure of Skp1tr-F-box$^{Fbw7}$-Ubv.Fw7.1 complex highlighting positions of loops deleted in Skp1tr. Positions that showed different preferences in Ubv selected against Skp1-F-box$^{Fbw7}$ versus parental Ubv.Fw7.1 sequence are shown as grey spheres. Position 75 was not defined in the structure and its projected location is shown.

To confirm that Ubv.Fw7.1 and Cul1 target overlapping sites on the Skp1-Fbw7 complex, we tested whether Ubv.Fw7.1 can inhibit Cul1 binding and SCF$^{Fbw7}$ ligase activity. Cul1 has been reported to bind to Skp1-Fbw7 in vitro with picomolar affinity (Pierce, 2013). With surface plasmon resonance (SPR) analysis, we confirmed this tight interaction between Cul1 and Skp1-F-box$^{Fbw7}$ (FIG. 6B) but we found that the interaction with Skp1tr-F-box$^{Fbw7}$ was ~1000-fold weaker (FIGS. 6A, C and D). Thus, we used in vitro assays with Skp1tr-Fbw7 to show that Ubv.Fw7.1 inhibits the polyubiquitination activity of SCF$^{Fbw7}$ (FIG. 6E) and Cul1 binding (FIG. 6F). We speculated that this mode of inhibition could be applied to other SCF ligases, prompting us to further characterize Ubv.Fw7.1 binding parameters with the ultimate goal of targeting other F-box proteins through the same mechanism.

Optimization of Ubvs for Binding to the Skp1-Fbw7 Complex

Figure 5:
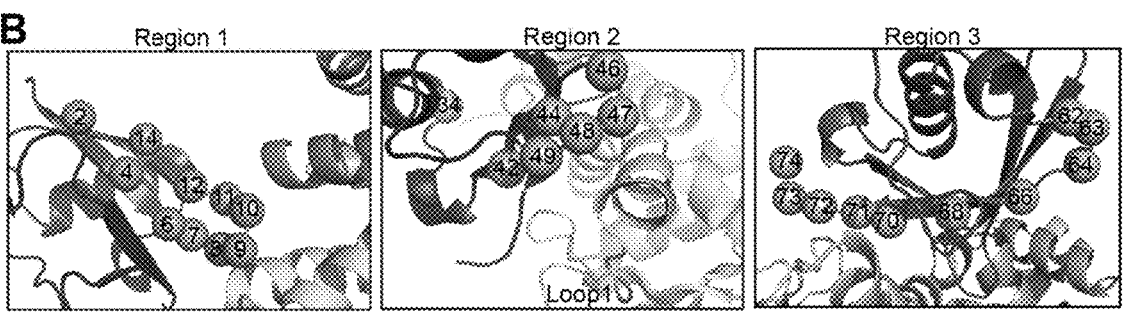
FIG. 5. Ubv libraries. (A) Regions 1, 2 and 3 targeted in the library designs are shown. Only positions relevant to the library design are included and residues that differ from wt Ub sequence are highlighted in grey. Positions subjected to soft-randomization are boxed and positions subjected to complete randomization are indicated by X. (B) Skp1tr-F-box$^{Fbw7}$-Ubv.Fw7.1 complex showing Ub positions diversified in the libraries. Regions 1, 2, and 3 are shown in separate panels and targeted positions are shown as grey spheres and numbered. Skp1tr and F-box$^{Fbw7}$ are shaded light grey and Ubv is shaded dark grey. Loop1 deleted in Skp1tr is indicated.

Ubv.Fw7.1 was selected for binding to a Skp1tr-Fbw7 complex that contained a truncated form of Skp1 optimized for structural analysis. However, our ultimate goal was to develop inhibitors of endogenous SCF ligases, and Ubv.Fw7.1 bound only weakly to the Skp1-F-box$^{Fbw7}$ complex containing full-length Skp1 (FIG. 3A), presumably due to unfavorable interactions with a negatively-charged loop near the N-terminus of Skp1 (FIGS. 6A, G and H). To engineer Ubvs with enhanced affinity for the Skp1-F-box$^{Fbw7}$ complex, we designed a second-generation library (Library 2) based on the sequence of Ubv.Fw7.1. Three residues involved in favorable contacts were held constant (Gly-8, Arg-10, Thr-11) while the remaining residues in contact with the Skp1tr-F-box$^{Fbw7}$ complex were "soft randomized" using a mutagenesis strategy that favored the parental sequence but allowed for an ~50% mutation frequency (FIG. 5). Following selections for binding to the Skp1-F-box$^{Fbw7}$ complex, 14 unique Ubvs were purified and ELISAs showed dramatically improved affinities in comparison with Ubv.Fw7.1 (FIG. 3A).

Many of the improved variants shared an A12G substitution and a preference for Arg at positions 49 and 75, and some also shared an I42R substitution (FIG. 3A). While preference for Gly at position 12 is probably due to optimization of Ubv interaction with the Skp1-Fbw7 interface, Arg substitutions at positions 42, 49 and 75 can be rationalized by the presence of a negatively-charged loop in full-length Skp1, which should come in contact with residues at these positions and would thus favor the accumulation of positive charge in the Ubvs (FIG. 6H). Ubv.Fw7.5, the tightest binder to Skp1-F-box$^{Fbw7}$, exhibited an IC$_{50}$ of 45 nM and we focused on this variant for further characterization.

Ubv.Fw7.1 and its relatives bind to the Skp1-Fbw7 complex mainly through contacts with Skp1, raising the possibility that these Ubvs may exhibit cross-reactivity with at least some of the many different human Skp1-F-box complexes. Thus, we tested the binding of Ubv.Fw7.5 to six Skp1-F-box domain complexes and, compared with Fbw7, we observed weaker but significant binding to three of these (Fbw2, Fbl1 and Fbw5). The affinities correlated with the degree of sequence similarity with the Fbw7 Ubv-binding region (FIG. 3B). Fbw2, which shares the highest homology with Fbw7 exhibited an 8-fold lower affinity, while Fbw5 which shows the least homology exhibited more than 50-fold lower affinity. The three F-box domains that did not bind to Ubv.Fw7.5 (Fbw1, Fbw11, and Fbw12) showed the least homology with Fbw7.

Structure-Based Selection of Ubvs that Bind Specifically to the Skp1-F-box$^{Fbw11}$ Complex Since contacts with F-box$^{Fbw7}$ are mediated entirely by the Region 1 loop of Ubv.Fw7.1, we considered whether sequence and length diversity in this loop could be exploited to alter specificity in favor of particular Skp1-F-box complexes. To explore this possibility, we designed a phage-displayed library (Library 3) in which four residues in Region 1 of Ubv.Fw7.5 were replaced by completely random sequences ranging from 11 to 13 residues in length to increase the size of the potential interaction interface with the F-box domain (FIG. 5). Library 3 was selected for binding to the Skp1-F-box$^{Fbw11}$ complex to determine whether this approach could be used to alter the F-box domain preference of Ubv.Fw7.5. Sequencing of 44 binding clones revealed that 42 were identical and contained a 12-residue insertion in Region 1 (FIG. 3C, Ubv.Fw11.1). Remarkably, purified Ubv.Fw11.1 protein was highly specific for Skp1-F-box$^{Fbw11}$, as it bound very weakly to Skp1 in complex with homologue F-box$^{Fbw1}$ (89% sequence identity) and did not bind detectably to any of the other five Skp1-F-box complexes that we tested (FIG. 3B). To further improve affinity, we designed a library (Library 4) in which Region 1 of Ubv.Fw11.1 was soft randomized, and binding selections yielded 16 unique Ubvs containing one to three substitutions (FIG. 7). Four of these variants exhibited enhanced affinities for the Skp1-F-box$^{Fbw11}$ complex (FIG. 3C) and the best of these (Ubv.Fw11.2) retained high specificity (FIG. 3B).

Intracellular Activity of Ubvs Targeting Fbw7 and Fbw11 Complexes

Figure 4:
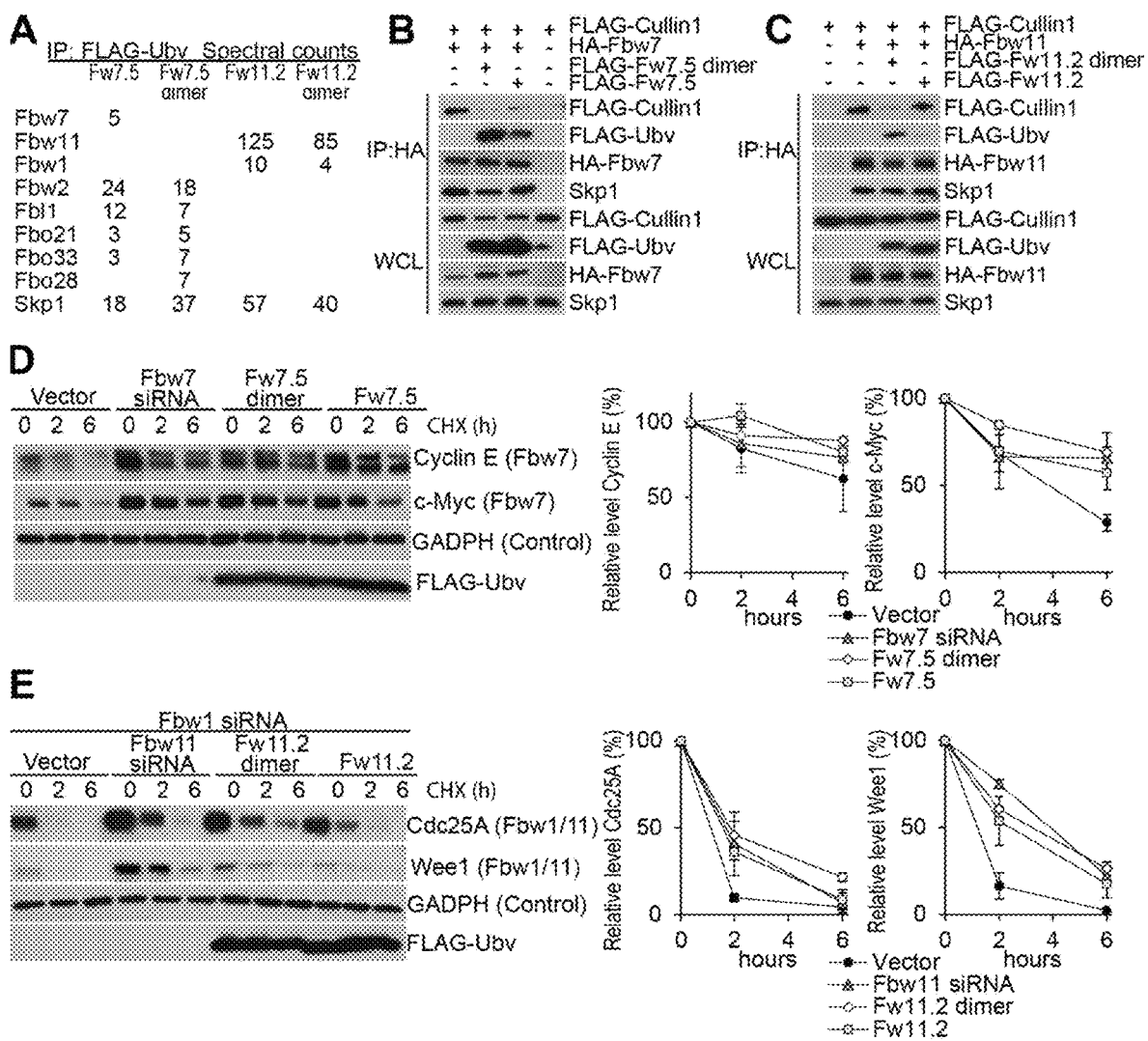
FIG. 4. Biological activity of Ubvs in HEK293T cells. (A) Ubv interaction partners identified by mass spectrometry of FLAG-Ubv immunoprecipitates from cell lysates. Spectral count refers to the number of peptides corresponding to each identified protein. Only proteins relevant to SCF ligases are shown (see Table 4 for complete list of detected proteins). (B) Expression of Fw7.5 Ubv in monomer or dimer disrupts interaction of Fbw7 with Cul1. HA-Fbw7 immunoprecipitates were probed for FLAG-Cul1 and endogenous Skp1, in the absence or presence of FLAG-Ubv expression. (C) Expression of Ubv.Fw11.2 Ubv in dimer format, but not monomer format, disrupts interaction between Fbw11 and Cul1. Analysis performed as described in (B). (D) and (E) Expression of Ubv.Fw7.5 (D) and Ubv.Fw11.2 (E) in monomer or dimer format stabilizes the SCF$^{Fbw7}$ (Cyclin E and c-Myc) and SCF$^{Fbw11}$ (Cdc25A and Wee1) substrates respectively. Cells were transiently transfected with either siRNA molecules (positive control), empty vector (Vector), or vectors expressing FLAG-Ubv. Cells were treated with Cycloheximide (CHX) for the indicated time points and cell lysates were probed with antibodies against the indicated proteins. Quantification of relative substrate levels was performed using ImageJ and represents average of two independent experiments (FIG. 4D, 8C for c-Myc and Cyclin E and FIG. 4E, 8D for Cdc25A and Wee1). (E) The effect of Fbw11 siRNA treatment and Ubv.Fw11.2 expression was assessed in the background of Fbw1 siRNA treatment.

We transiently expressed Ubv.Fw7.5 or Ubv.Fw11.2 in HEK293T cells to ascertain whether these Ubvs were able to exert effects in live cells. Since Fbw7 and Fbw11 protein complexes function as dimers (Suzuki, 2000; Welcker, 2013), expression vectors were designed to express Ubvs either as monomers or as dimers held together by a homodimeric GCN4 leucine zipper to enhance effective affinities through avidity (Table 2) (Harbury, 1993). To examine the interactions of Ubvs with endogenous proteins, Ubvs were immunoprecipitated, and co-precipitated proteins were identified by mass spectrometry (FIG. 4A). Consistent with the in vitro specificity profiles (FIG. 3B), Ubv.Fw7.5 co-immunoprecipitated Fbw7 and Skp1, and also several other F-box proteins including Fbw2 and Fbl1. Fbw7 was detected with the lowest spectral counts among the F-box proteins, but this is likely due to low expression levels of endogenous Fbw7. In support of this, a significant amount of Fbw7, but not Fbl1, co-immunoprecipitated with Ubv.Fw7.5 in cells overexpressing Fbw7 or Fbl1 (FIG. 8A). In contrast, Ubv.Fw11.2 was very specific for Fbw11, co-immunoprecipitating only Skp1, Fbw11 and small amounts of Fbw1. Similar levels of interacting proteins were detected whether Ubvs were expressed as monomers or dimers, but Ubv dimers co-immunoprecipitated more non-specific proteins involved in cell housekeeping functions (Table 4).

To determine whether Ubvs are able to disrupt interactions between Cul1 and Skp1-F-box complexes in cells, exogenously expressed Fbw7 or Fbw11 was immunoprecipitated in the absence or presence of Ubv. Expression of Ubv.Fw7.5 monomer or dimer significantly reduced or completely abrogated the co-immunoprecipitation of Cul1 with Fbw7, respectively, but did not affect co-immunoprecipitation of Skp1 (FIG. 4B). In the case of Ubv.Fw11.2, expression of the dimer, but not the monomer, caused significant reduction in the amount of Cul1 (but not Skp1) that co-immunoprecipitated with Fbw11, and this was consistent with the fact that the dimer but not the monomer co-immunoprecipitated with Fbw11 (FIG. 4C). Thus, co-immunoprecipitation assays show that both Ubv.Fw7.5 and Ubv.Fw11.2 interfere with the interactions between Skp1-F-box complexes and Cul1 in cells but do not affect interactions between Skp1 and F-box proteins, although dimerization is required to observe this effect in the case of Ubv.Fw11.2.

In order to determine whether cellular expression of Ubv.Fw7.5 or Ubv.Fw11.2 led to inhibition of their corresponding ligases, we analyzed the stability of ligase substrates. Expression of Ubv.Fw7.5 in either monomeric or dimeric format increased protein levels and decreased degradation rate of the SCF$^{Fbw7}$ substrates Cyclin E and c-Myc to levels comparable with those observed upon expression of an siRNA targeting Fbw7 but had no effect on substrates of other SCF ligases, demonstrating that the observed inhibition was specific (FIG. 4D, 8C). In the case of Ubv.Fw11.2, assays were performed in the presence of an siRNA targeting Fbw1 to reduce levels of SCF$^{Fbw1}$ (FIG. 8B), which shares substrates with SCF$^{Fbw11}$. Expression of the Ubv.Fw11.2 dimer and monomer increased the abundance and decreased the degradation rate of the SCF$^{Fbw11}$ substrates Cdc25A and Wee1, which was similar to stabilization observed upon expression of an siRNA targeting Fbw11 (FIG. 4E). Expression of the Ubv.Fw11.2 monomer had a smaller effect, consistent with the dimer being much more effective than the monomer in disruption of the interaction between Cul1 and the Skp1-Fbw11 complex (FIG. 4C). The inhibitory effect of Ubv.Fw11.2 was specific to SCF$^{Fbw11}$, as it did not affect substrates of other SCF ligases (FIG. 8D) and it did not stabilize substrates of Fbw1/11 in the background of Fbw11 siRNA treatment (FIG. 8E). Since Fbw7 and Fbw11 are involved in cell cycle progression (Wang, 2014), we also tested whether inhibition of these E3 ligases by Ubvs exerts any effect on cell cycle. While we did not detect any large effects, the small changes that were observed (decrease in G1 population for Ubv.Fw7.5 and increase in G2/M population for Ubv.Fw11.2) (FIGS. 8F and G) were similar to those obtained with siRNA treatment and consistent with the previously reported effects of Fbw7 (Wu, 2015) and Fbw11 inhibition (Guardavaccaro, 2003). Taken together, these data show that engineered Ubvs in cells interact with endogenous Skp1-F-box complexes in cells and cause displacement of Cul1 and consequent inhibition of specific SCF E3 ligases.

Materials and Methods

Protein Expression and Purification.

His-tagged Fbw7 and GST-tagged Skp1 were co-expressed from dicistronic mRNA. Ubvs and Cul1 N-terminal domain (NTD) were expressed with His-FLAG tag. See Table 2 for detailed list of all expression constructs. All proteins were expressed in *Escherichia coli* BL21 (pLys) cells, which were grown to $OD_{600}$ 0.6-1.0 and induced with 1 mM IPTG either overnight at 16° C. (for Skp1-F-box complexes and Cul1 NTD) or for 3 hours at 37° C. (for Ubvs). Cells were lysed and proteins were purified by Ni-NTA chromatography using standard techniques. Since expression of Skp1 was higher than expression of F-box proteins, purifying Skp1-F-box complexes through His-tagged F-box proteins ensured that only complexes were purified. Eluted proteins were dialyzed into 50 mM Hepes, pH 7.5, 500 mM NaCl, 10% glycerol, 1 mM DDT buffer and stored at 4° C. or frozen at −80° C. for further applications.

Phage-Displayed Ubv Library Design and Construction.

Library 1 in this study is the same as Library 2 in a previous study (Ernst). Libraries 2, 3 and 4 in this study were constructed using methods described previously (Fellouse, 2007). For the construction of Library 2, a phagemid designed for the phage display of Ub (Ernst) was subjected to site-directed mutagenesis with degenerate oligonucleotides to simultaneously mutate three regions in the gene encoding for Ub. Positions were diversified with a "soft randomization" strategy (Sidhu, 2000), in which the nucleotide ratio at degenerate positions was adjusted to 70% of the wt nucleotide and 10% of each of the other nucleotides. See FIG. 5 for original sequence and positions targeted for diversification, and Table 5 for oligonucleotides used for library construction. For the construction of Libraries 3 and 4, a phagemid was designed for the display of an Ub variant in which positions 1-35 were wt sequence and positions 42-76 were the sequence of Ubv.Fw7.5. For the construction of Library 3, a set of mutagenic oligonucleotides was used to replace Ub positions 8-11 with completely random sequences containing 11-13 residues (FIG. 5, Table 5). For the construction of Library 4, a mutagenic oligonucleotide was used to replace positions 8-11 with a soft-randomized sequence corresponding to the sequence of Ubv.Fw11.1 (FIG. 5, Table 5). The diversities of the constructed libraries were as follows: Library 2, $2.2 \times 10^9$; Library 3, $5.0 \times 10^9$; Library 4, $1.5 \times 10^9$.

Selection of Ubv Variants.

GST-tagged target proteins (GST-Skp1:His-F-box) were coated on 96-well MaxiSorp plates (Thermoscientific 12565135) by adding 100 µL of 1 µM proteins and incubating overnight at 4° C. Five rounds of binding selections with phage library pools were performed against immobilized proteins as described (Fellouse, 2007). To eliminate Ubv-phage that bound nonspecifically, input phage pools were either mixed with non-target proteins (round 1) or pre-incubated on plates coated with non-target proteins (rounds 2-5). The non-target proteins were GST for selections with Libraries 1 and 2 or a mix of non-target Skp1-F-box complexes for selections with Libraries 3 and 4.

ELISAs.

GST-tagged target proteins were immobilized on 384-well MaxiSorp plates (Thermoscientific 12665347) by adding 30 µL of 1 µM proteins for overnight incubation at 4° C. or for 2 hour incubation at room temperature. Phage and protein ELISA against immobilized proteins were performed as described (Fellouse, 2007), except that three washes were performed for all wash steps and volumes were scaled down from 100 µL to 30 µL to accommodate the 384-well format. Binding of phage was detected using anti-M13-HRP antibody (1:5000 dilution, GE Healthcare 27-9421-01) and binding of FLAG-tagged ligands (Ubv or Cul1) was detected using anti-FLAG-HRP antibody (1:5000 dilution, Sigma A8592). To measure protein ELISA $EC_{50}$ values, the concentration of ligand proteins (Ubv or Cul1) was varied, while the concentration of target proteins (GST-Skp1:His-F-box) immobilized on the plate remained constant. $EC_{50}$ values were calculated by fitting the obtained binding curves to four parameter logistic non-linear regression model and corresponded to ligand concentration (curve inflection point) at which 50% of binding was observed. To measure protein ELISA $IC_{50}$ values, the concentration of target in solution (Skp1-F-box) was varied, while the concentration of target immobilized on the plate (GST-Skp1:His-F-box) and concentration of ligand (Ubv) in solution remained constant. $IC_{50}$ values, which corresponded to the concentration of target in solution which inhibited 50% of ligand binding to the immobilized target, were calculated by fitting the data as described for $EC_{50}$ values.

Surface Plasmon Resonance Analysis.

SPR measurements were performed at 25° C. using ProteOn XPR36 instrument (Bio-Rad). Skp1tr-F-box$^{Fbw7}$ and Skp1-F-box$^{Fbw7}$ ligands were immobilized by amine coupling to GLC sensor chip surface. Cul1 NTD was diluted into PBT buffer (phosphate buffered saline, 0.05% Tween, and 0.5% BSA) and injected for 360 sec at 50 µL/min. Dissociation was monitored for 1200 sec in PBT buffer. Sensorgrams were fitted to 1:1 Langmuir model using ProteOn Manager Software (Bio-Rad).

Protein Purification for Crystallization and Structure Determination.

Complex consisting of GST-tagged Skp1tr and His-tagged F-box$^{Fbw7}$ was purified on Ni-NTA resin from cells co-expressing both proteins (see Table 2 for constructs used). To remove GST and His purification tags (containing TEV protease cleavage sites) the obtained complex was first bound to glutathionine resin, next eluted from the resin by TEV cleavage of GST tag and finally re-purified on Ni-NTA resin to remove His-tagged TEV protease and other impurities. Similarly, His-tagged Ubv.Fw7.1 was purified on Ni-NTA resin, His tag (containing TEV protease cleavage site) was removed by TEV protease and cleaved Ubv was re-purified on Ni-NTA resin. Cleaved Skp1tr-F-box$^{Fbw7}$ complex was mixed with excess of cleaved Ubv.Fw7.1 and subjected to gel filtration chromatography. A single peak corresponding to Skp1tr-F-box$^{Fbw7}$-Ubv.Fw7.1 complex was collected, exchanged into 20 mM Hepes pH 7.5, 200 mM NaCl, 1 mM DTT buffer, and concentrated to 19 mg/ml. Crystals were grown by mixing equal volumes of Skp1-F-box$^{Fbw7}$-Ubv.Fw7.1 solution with the reservoir solution (100 mM acetate pH 4.5, 12% PEG 4000, 15% glycerol) and incubating at 20° C. The crystals were cryoprotected by soaking in reservoir solution with a final glycerol concentration of 20%. Data was collected at NE-CAT 24 ID-C (APS, Chicago, Ill.) and processed with HKL2000 (Otwinowski, 1997). The structure was solved by molecular replacement with Phaser (McCoy, 2007) using structures of Skp1tr-Fbw7 (PDB:2OVR) and ubiquitin (PDB:1 UBQ) as search models. The model was rebuilt using Coot (Emsley, 2004) and refined to 2.5 Å with a working $R_{value}$ of 20.0% and $R_{free}$ of 25.0% using PHENIX (Adams, 2010).

Protein Expression Constructs Used in Cell-Based Assays.

Genes encoding for FLAG-tagged Ubvs were cloned into pcDNA3.1/nFLAG-Dest vector for monomer expression or into the same vector modified to encode a GCN4 leucine zipper dimerization sequence (RMKQLEDKIEELLSKI-YHLENEIARLKKLIGER) inserted in place of vector nucleotides 944-976) for dimer expression. Cul1, Fbw11, Fbw1 and Fbw7 were expressed from pcDNA3.1 based vectors (See Table 2 for additional details).

Cell-Based Functional Assays.

On day 0, 6-well plates were seeded with $4 \times 10^5$ HEK293T cells. On day 1, cells were transfected with 2 µg of plasmid DNA (empty vector, various FLAG-Ubv or various FLAG-F-box constructs) using the X-tremeGENE transfection reagent (Roche 06365809001), according to manufacturer's protocol. After 6 hours, media was removed and replaced with fresh media, and cells were subjected to a second round of transfection with 10 nM siRNA (Control, Fbw1, Fbw11, Fbw1+Fbw11 or Fbw7) using Lipofectamine RNAiMAX (Invitrogen 13778-075), according to manufacturer's instructions. siRNA included the following: Silencer Select Negative Control #1 (Invitrogen 4390843); Fbw1: CGGAAGAGUUUUUCGACUAtt (Invitrogen 17110); Fbw11: GGUUGUUAGUGGAUCAUCAtt (Invitrogen s23485); Fbw7: CGGGUGAAUUUAUUCGAAAtt (Invitrogen s30665).

On day 2, media was replaced with fresh media. On day 3, cycloheximide (100 µg/ml) was added for 0-6 hours. Cells were lysed in lysis buffer (Cell Signalling 9803) and cell lysates were subjected to western blot analysis with antibodies against endogenous proteins (Cdc25A (Upstate 05-743), Wee1 (Cell Signaling 4936), c-Myc (Santa Cruz SC-40), Cyclin E (ABCAM 3927), p27 (BD Transduction Laborotories 610241), Cry2 (Abcam 93802), GADPH (Cell Signaling 2118L) or FLAG-tagged proteins (Sigma-Aldrich A8592)).

Flow Cytometry Analysis.

HEK293T cells were treated as described in Cell-based functional assays section. Two days post transfection, cells were re-suspended in phosphate buffered saline (PBS), fixed by addition of 70% ethanol and stored at −20° C. Immediately prior to flow cytometry analysis fixed cells were washed in PBS, re-suspended in 500 µL PBS at concentration of $1 \times 10^6$ cells/ml, and stained by addition of Hoechst 33342 (Life Technologies H3570) dye to final concentration of 4 µg/ml. Stained cells were analyzed by UV excitation at 355 nm on a BD LSRFortessa X-20 cell analyzer and detected using a 450/50 nm bandpass filter. The data acquired was analyzed by FlowJo10 software.

Immunoprecipitation Assays.

HEK293T cells were grown to 70-80% confluency on 10-cm plates and transfected with 10 µg total plasmid DNA (HA-F-box, FLAG-Ubv, FLAG-Cullin1, empty vector or various combinations) using the X-tremeGENE 9 transfection reagent (Roche 06365809001) according to manufactures instructions. Cells were harvested 2 days post transfection and cell pellets were frozen for further applications. For co-immunoprecipitation analysis, cells were re-suspended in 1 ml lysis buffer (25 mM Tris pH 7.5, 150 mM NaCl, 1 mM EDTA, 1% NP-40, 5% glycerol, protease inhibitor cocktail (Sigma S8830)), and after 1 h incubation at 4° C., cell lysate was clarified by centrifugation at 15000 rpm for 10 min. 800 µg of total cell lysate was incubated with 3 µg of anti-FLAG (Sigma F1804) or anti-HA (Sigma 3663) antibody overnight at 4° C. Immunoprecipitations were performed using Protein A/G Agarose (Thermo Scientific™ Pierce 20422) according to manufacturer's protocol. Immunoprecipitated proteins were visualized by western blot using anti-FLAG-HRP (Sigma A8592), anti-HA-HRP (Sigma H6533), and anti-Skp1 (Abcam 10536) antibodies.

Mass Spectrometry Analysis.

Frozen cell pellets were thawed into 1 ml High Salt AFC buffer (10 mM Tris-HCl pH7.9, 420 mM NaCl, 0.1% NP-40, 1 mM sodium orthovanadate, 2 mM sodium pyrophosphate, 10 mM NaF, protease inhibitor cocktail (Sigma S8830)). Cell suspensions were then were subjected to 3 freeze-thaw cycles, sonicated (5 cycles of 0.3 sec on and 0.7 sec off) and incubated for 30 min at 4° C. with 12.5-25 U of benzonase nuclease (Sigma E1014). The samples were centrifuged at 13,000 rpm for 30 min at 4° C. and 10 µl slurry of M2 anti-Flag beads (Sigma 8823) was added for overnight incubation. Beads were washed 2 times with low salt AFC buffer (10 mM Tris-HCL, pH7.9, 100 mM NaCl, 0.1% NP-40) and 3 times with low salt AFC buffer without detergent. Immunoprecipitated proteins were eluted from the beads with 0.5 M ammonium hydroxide, 4×50 µl for a total of 200 µl. Samples were snap frozen in liquid nitrogen and dried. Further preparation of samples, mass spectrometry and analysis of obtained data was performed as previously described (Marcon, 2014).

TABLE 2

Protein expression vectors

| Constructs | Protein residues [a] | Vector | N- terminus | Tag residues [b] |
|---|---|---|---|---|
| Bacterial vectors | | | | |
| Fbw7 (F-box-WD40) | 263-708 | pPROEX | His-TEV | MSYYHHHHHHDYDIPTT |
| Fbw7 F-box | 263-367 | HTb | | ENLYF*QGA |
| Fbw7 F-box (Structure) | 263-323 | | | |
| Fbw2 F-box | 53-104 | | | |
| Fbw5 F-box | 1-79 | | | |
| Fb11 F-box | 95-139 | | | |
| Fbw12 F-box | 1-49 | | | |
| Fbw1 F-box | 101-214 | | | |
| Fbw11 F-box | 80-191 | | | |
| Skp1 | Full length | pPROEX | GST-TEV | GST-DYDIPTTENLYFQ*GA |
| Skp1 (Loop 1Δ) | 38-43Δ 70-77Δ, | HTb | | |

TABLE 2-continued

Protein expression vectors

| Constructs | Protein residues [a] | Vector | N- terminus | Tag residues [b] |
|---|---|---|---|---|
| Skp1 (Loop 2Δ) | K78G E79s K80G R81G | | | |
| Skp1tr (ELISA/Structure) | 38-43Δ 70-77Δ, K78G E79S K80G R81G | | | |
| CuL1 NTD [c] | 1-410 (V367D L371E) | P11 | His-TEV-FLAG | MGSSHHHHHHSSGRENLYFQ* GHMDYKDDDDK |
| Ubv.Fw7.1 (Structure) | 1-76 | p53DEST | His-TEV | MAHHHHHHVTSLYKKAG ENLYFQ*GSGS |
| Ubv (ELISA) | Full length | p53DEST | His-FLAG | MAHHHHHHVTSLYKKAG DYKDDDDK |
| Mammalian vectors | | | | |
| FLAG-Ubv monomer | Full length | pcDNA3.1/ nFLAGDEST | FLAG-Linker-FLAG | MDYKDDDKGQGPDPSTNSADI TSLYKKAGTMDYKDDDDK |
| FLAG-Ubv Leu-zipper dimer | Full length | pcDNA3.1/ nFLAGDEST (+Leu-zipper) | FLAG-Leu Zipper-FLAG | MDYKDDDKGQ RMKQLEDKIEELLSKIYHLENE IARLKKLIGERTSLYKKAGTMD YKDDDDK |
| HA-Fbw7 HA-Fbw11 (Isoform B) | Full length | pcDNA3.1/ nHADEST | HA | MYPYDVPDYAGQG PDPSTNSADITSLYKKAGST |
| FLAG-Cul1 FLAG-Fbw7 FLAG-Fbw11 (Isoform B) | Full length | pcDNA3.1/ nFLAGDEST | FLAG | MDYKDDDDKGQGPDPSTNSA DITSLYKKAGT |
| FLAG-Fbw1 | Full length | pcDNA3 | FLAG | MDYKDDDDK |

[a] Residue limits of canonical human isoforms. Any amino acid substitutions relative to wt are indicated if present.
[b] Tag residues are shown, except for GST tag. Residues that comprise functional elements are underlined and TEV cleavage site denoted by *. All tags are N-terminal.
[c] Cul1 N-terminal domain (NTD) was expressed with V376D and L317E substitutions that are necessary for solubility in the absence of the C-terminal domain as described (Zheng, 2002).

TABLE 3

Data collection and refinement statistics for Skp1tr-F-box$^{Fbw7}$-Ubv.Fw7.1 Complex

| Data collection | |
|---|---|
| Space group | $P2_12_12_1$ |
| Cell dimensions | |
| a, b, c (Å) | 63.4, 98.0, 107.7 |
| α, β, γ (°) | 90, 90, 90 |
| Resolution (Å) | 50.0-2.5 (2.56-2.50)[a] |
| $R_{meas}$ | 0.052 (0.359) |
| I/σI | 19.6 (1.3) |
| Completeness (%) | 99.4 (99.1) |
| Redundancy | 4.4 (3.9) |
| Refinement | |
| Resolution (Å) | 50.0-2.5 (2.56-2.50) |
| No. reflections | 23612 (1532) |
| $R_{work}/R_{free}$ | 20.0/24.0 (30.9/39.4) |
| No. atoms | |
| Protein | 4246 |
| Water | 38 |
| B-factors | |
| Protein | 81.1 |
| Water | 51.2 |
| R.m.s. deviations | |
| Bond lengths (Å) | 0.004 |
| Bond angles (°) | 0.879 |
| Ramachandran | |
| favored | 97.6 |
| allowed | 2.4 |
| outliers | 0 |

[a] Values in parenthesis correspond to the highest shell.

TABLE 4

Mass spectrometry analysis of Ubv interactions in HEK293T cells

| ID[a] | Gene[b] | Description | V[c] | Ub[c] | Fw7.5 | Fw7.5 dimer | Fw11.2 | Fw11.2 dimer |
|---|---|---|---|---|---|---|---|---|
| | | All Ubv | | | | | | |
| P63208 | SKP1 | Skp1 | 0[d] | 0 | 18 | 37 | 57 | 40 |
| P68363 | TUBA1B | Tubulin | 21 | 12 | 21 | 66 | 36 | 2 |
| Q09028 | RBBP4 | Histone binding | 2 | 0 | 0 | 12 | 0 | 0 |
| P53671 | LIMK2 | Histone kinase | 0 | 0 | 10 | 10 | 8 | 5 |
| Q9H479 | FN3K | Ketosamine-3-kinase | 0 | 0 | 9 | 0 | 4 | 0 |
| O15018 | PDZD2 | PDZ domain containing | 0 | 0 | 2 | 5 | 5 | 1 |
| Q8NI27 | THOC2 | mRNA processing | 0 | 0 | 5 | 5 | 0 | 3 |
| | | Monomer Ubv specific | | | | | | |
| O95479 | H6PD | Glucose dehydrogenase | 0 | 0 | 203 | 0 | 143 | 0 |
| Q9UIV8 | PI13 | Peptidase inhibitor | 0 | 0 | 146 | 0 | 120 | 0 |
| Q96QC0 | PPP1R10 | Phosphatase | 0 | 0 | 6 | 0 | 6 | 0 |
| | | Dimer Ubv specific | | | | | | |
| Q15233 | NONO | mRNA processing | 0 | 0 | 0 | 118 | 3 | 114 |
| Q8WXF1 | PSPC1 | mRNA processing | 3 | 0 | 0 | 56 | 0 | 51 |
| P23246 | SFPQ | mRNA processing | 5 | 2 | 0 | 60 | 2 | 70 |
| Q15691 | MAPRE1 | Microtubule binding | 0 | 0 | 0 | 58 | 0 | 48 |
| P17980 | PSMC3 | 26S proteasome subunit | 0 | 0 | 0 | 39 | 0 | 37 |
| Q9P2E9 | RRBP1 | Ribosome receptor | 0 | 0 | 0 | 13 | 0 | 28 |
| Q9Y490 | TLN1 | Cytoskeletal component | 0 | 0 | 2 | 38 | 0 | 10 |
| P42566 | EPS15 | EGFR substrate | 0 | 0 | 0 | 20 | 0 | 27 |
| Q9UII2 | ATPIF1 | ATPase inhibitor | 0 | 0 | 0 | 27 | 0 | 19 |
| O00233 | PSMD9 | 26S proteasome subunit | 0 | 0 | 0 | 14 | 0 | 21 |
| P05787 | KRT8 | Keratin | 0 | 0 | 0 | 20 | 0 | 18 |
| Q16204 | CCDC6 | Unknown | 0 | 0 | 0 | 18 | 0 | 13 |
| Q15019 | SEPT2 | Cytoskeletal GTPase | 0 | 0 | 0 | 15 | 0 | 10 |
| Q14203 | DCTN1 | Microtubule transport | 0 | 0 | 0 | 9 | 0 | 17 |
| P46736 | BRCC3 | Lys-63 deubiquitinase | 0 | 0 | 0 | 15 | 0 | 16 |
| P80303 | NUCB2 | Calcium homeostasis | 0 | 0 | 0 | 8 | 0 | 14 |
| Q07065 | CKAP4 | Cytoskeleton associated | 0 | 0 | 0 | 14 | 0 | 12 |
| P31146 | CORO1A | Cytoskeletal component | 0 | 0 | 0 | 12 | 0 | 7 |
| O60271 | SPAG9 | Scaffold protein | 0 | 0 | 0 | 9 | 0 | 13 |
| Q9BW19 | KIFC1 | Microtubule transport | 0 | 0 | 0 | 5 | 0 | 13 |
| P16220 | CREB1 | Transcription factor | 0 | 0 | 0 | 8 | 0 | 10 |
| Q13625 | TP53BP2 | p53 regulator | 0 | 0 | 0 | 5 | 0 | 8 |
| O00139 | KIF2A | Microtubule transport | 0 | 0 | 0 | 9 | 0 | 7 |
| O43293 | DAPK3 | Serine/Threonine kinase | 0 | 0 | 0 | 9 | 0 | 6 |
| Q9NVA2 | SEPT 11 | Cytoskeletal GTPase | 0 | 0 | 0 | 8 | 0 | 9 |
| Q13976 | PRKG1 | Serine/Threonine kinase | 0 | 0 | 0 | 7 | 0 | 9 |
| Q14141 | SEPT6 | Cytoskeletal GTPase | 0 | 0 | 0 | 4 | 0 | 8 |
| Q9P0K7 | RAI14 | Actin associated | 0 | 0 | 0 | 2 | 0 | 7 |
| Q16181 | SEPT7 | Cytoskeletal GTPase | 0 | 0 | 0 | 10 | 0 | 10 |
| Q14980 | NUMA1 | Nuclear matrix | 0 | 0 | 0 | 4 | 0 | 10 |
| Q96CN9 | GCC1 | Golgi associated | 0 | 0 | 0 | 4 | 0 | 7 |
| P40222 | TXLNA | Vesicle traffic | 0 | 0 | 0 | 3 | 0 | 7 |
| O95396 | MOCS3 | tRNA biosynthesis | 0 | 0 | 0 | 2 | 0 | 7 |
| Q9UPY8 | MAPRE3 | Microtubule associated | 0 | 0 | 0 | 2 | 0 | 7 |
| P62195 | PSMC5 | 26S proteasome subunit | 0 | 0 | 0 | 6 | 0 | 3 |
| Q8N302 | AGGF1 | Angiogenic factor | 0 | 0 | 0 | 2 | 0 | 6 |
| Q15390 | MTFR1 | Mitochondrial fission | 0 | 0 | 0 | 0 | 0 | 6 |
| O75146 | HIP1R | Clathrin associated | 0 | 0 | 0 | 5 | 0 | 3 |
| P53621 | COPA | Golgi-to-ER transport | 0 | 0 | 0 | 5 | 0 | 2 |
| O60308 | KIAA0562 | Centrosomal protein | 0 | 0 | 0 | 5 | 0 | 2 |
| Q969V6 | MKL1 | Transcription factor | 0 | 0 | 0 | 4 | 0 | 5 |
| Q15007 | WTAP | mRNA processing | 0 | 0 | 0 | 2 | 0 | 5 |
| Q8TBA6 | GOLGA5 | Golgi formation | 0 | 0 | 0 | 2 | 0 | 5 |
| Q4VCS5 | AMOT | Tight junction maintenance | 0 | 0 | 0 | 0 | 0 | 5 |
| Q9H6D7 | HAUS4 | Spindle assembly | 0 | 0 | 0 | 0 | 0 | 5 |
| | | Ubv.Fw11.2 specific | | | | | | |
| Q9UKB1 | FBXW11 | F-box | 0 | 0 | 0 | 0 | 125 | 85 |
| Q9Y297 | FBXW1 | F-box | 0 | 0 | 0 | 0 | 10 | 4 |
| P0C0L4 | C4A | Complement comp. | 0 | 0 | 0 | 0 | 13 | 3 |
| Q06203 | PPAT | Ribosyl transferase | 0 | 0 | 0 | 0 | 13 | 3 |
| P04632 | CAPNS1 | Protease subunit | 0 | 0 | 0 | 0 | 12 | 0 |
| Q96K76 | USP47[e] | Ubiquitin protease | 0 | 0 | 0 | 0 | 3 | 7 |
| Q01664 | TFAP4 | Transcription factor | 0 | 0 | 0 | 0 | 6 | 0 |
| | | Ubv.Fw7.5 specific | | | | | | |
| Q9UKT8 | FBXW2 | F-box | 0 | 0 | 24 | 18 | 0 | 0 |
| P19838 | NFKB1 | Transcription Factor | 0 | 0 | 22 | 0 | 0 | 0 |
| Q13309 | SKP2 | F-box | 0 | 0 | 12 | 7 | 0 | 0 |

TABLE 4-continued

Mass spectrometry analysis of Ubv interactions in HEK293T cells

| ID[a] | Gene[b] | Description | V[c] | Ub[c] | Fw7.5 | Fw7.5 dimer | Fw11.2 | Fw11.2 dimer |
|---|---|---|---|---|---|---|---|---|
| Q7Z6M2 | FBXO33 | F-box | 0 | 0 | 3 | 7 | 0 | 0 |
| Q9NVF7 | FBXO28 | F-box | 0 | 0 | 0 | 7 | 0 | 0 |
| Q969H0 | FBXW7 | F-box | 0 | 0 | 5 | 0 | 0 | 0 |
| O94952 | FBXO21 | F-box | 0 | 0 | 3 | 5 | 0 | 0 |

[a]ID and
[b]Gene name for identified proteins showing >2-fold enrichment relative to control and 5 peptides or more in any of the Ubv samples.
[c]Controls corresponds to HEK293T cells transfected with empty vector [V] or Ub Δ75G76G (Ub).
[d]Numbers of endogenous peptides corresponding to the identified protein.
[e]USP47 is a known interactor of Fbw1 and Fbw11(Peschiaroli, 2010).

TABLE 5

Oligonucleotides used for construction of Ubv Libraries

| Oligo | Sequence[a] | Library |
|---|---|---|
| oMG210 | ATG CAG ATT TTC GTG (5)(5)(5) (5)(6)(6) GGT (7)(6)(5) CGT ACC (7)(6)(5) ATC ACC CTC GAG GT | 2 |
| oMG212 | AAG ATC CAG GAT AAG (7)(5)(5) GGA ATT CCT CCT GAT CAG CAG (5)(8)(8) CTG (5)(1)(1) TTT (8)(6)(6) (6)(7)(8) (5)(5)(7) (6)(8)(6) CTG GAA GAT GGA CGT | 2 |
| oMG214 | ATT CAA AAG GAG TCT (5)(6)(8) CTT (6)(7)(8) CTT (7)(8)(7) (8)(8)(7) (N5)(8)(8) (8)(8)(8) (6)(7)(8) (7)(7)(8) (7)(7)(8) GGC GGT GGC GGA TCC | 2 |
| oMG281 | ATT TTC GTG AAA ACCNNK NNK NNK NNK NNK NNK NNK NNK NNK NNK ACC ATC ACC CTC GAG | 3 |
| oMG282 | ATT TTC GTG AAA ACC NNK NNK NNK NNK NNK NNK NNK NNK NNK NNK NNK ACC ATC ACC CTC GAG | 3 |
| oMG283 | ATT TTC GTG AAA ACC NNK NNK NNK NNK NNK NNK NNK NNK NNK NNK NNK NNK ACC ATC ACC CTC GAG | 3 |
| oMG289 | ATTTTCGTGAAAACC (8)(5)(9) (6)(6)(6) (8)(5)(9) (5)(5)(5) (8)(6)(9) (7)(7)(8) (8)(6)(9) (8)(5)(9) (6)(5)(9) (5)(5)(9) (5)(5)(9) (8)(5)(9) ACCATCACCCTCGAG | 4 |

[a]Numbers denote specific nucleotide mixtures: 5 = 70% A and 10% other nucleotides; 6 = 70% C and 10% other nucleotides; 7 = 70% G and 10% other nucleotides; 8 = 70% T and 10% other nucleotides; 9 = 90% T and 10% G. "N" denotes an equimolar mixture of all four nucleotides. "K" denotes an equimolar mixture of G and T.

REFERENCES

Adams P D, et al. (2010) PHENIX: a comprehensive Python-based system for macromolecular structure solution. *Acta crystallographica. Section D, Biological crystallography* 66(Pt 2):213-221.

Bhowmick P, Pancsa R, Guharoy M, & Tompa P (Functional diversity and structural disorder in the human ubiquitination pathway. *PloS one* 8(5):e65443.

Emsley P & Cowtan K (2004) Coot: model-building tools for molecular graphics. *Acta crystallographica. Section D, Biological crystallography* 60(Pt 12 Pt 1):2126-2132.

Ernst A, et al. (A strategy for modulation of enzymes in the ubiquitin system. Science 339(6119):590-595.

Fellouse F A, Sidhu, S. S. (2007) Making antibodies in bacteria. *Making and Using Antibodies*, ed Howard G C, Kaser, M. S. (CRC Press, Boca Raton, Fla.), pp 157-180.

Guardavaccaro D, et al. (2003) Control of meiotic and mitotic progression by the F box protein beta-Trcp1 in vivo. *Developmental cell* 4(6):799-812.

Hao B, Oehlmann S, Sowa M E, Harper J W, & Pavletich N P (2007) Structure of a Fbw7-Skp1-cyclin E complex: multisite-phosphorylated substrate recognition by SCF ubiquitin ligases. *Molecular cell* 26(1):131-143.

Harbury P B, Zhang T, Kim P S, & Alber T (1993) A switch between two-, three-, and four-stranded coiled coils in GCN4 leucine zipper mutants. *Science* 262(5138):1401-1407.

Jin J, et al. (2004) Systematic analysis and nomenclature of mammalian F-box proteins. *Genes & development* 18(21):2573-2580.

Lee C V, et al. (2004) High-affinity human antibodies from phage-displayed synthetic Fab libraries with a single framework scaffold. *Journal of molecular biology* 340(5): 1073-1093.

Marcon E, et al. (2014) Human-chromatin-related protein interactions identify a demethylase complex required for chromosome segregation. *Cell reports* 8(1):297-310.

McCoy A J, et al. (2007) Phaser crystallographic software. *Journal of applied crystallography* 40(Pt 4):658-674.

Orlicky S, et al. (An allosteric inhibitor of substrate recognition by the SCF(Cdc4) ubiquitin ligase. *Nat Biotechnol* 28(7):733-737.

Otwinowski Z & Minor W (1997) Processing of X-ray diffraction data collected in oscillation mode. *Methods in enzymology* 276:307-326.

Pashkova N, et al. (2010) WD40 repeat propellers define a ubiquitin-binding domain that regulates turnover of F box proteins. *Molecular cell* 40(3):433-443.

Peschiaroli A, Skaar J R, Pagano M, & Melino G (2010) The ubiquitin-specific protease USP47 is a novel beta-TRCP interactor regulating cell survival. *Oncogene* 29(9):1384-1393.

Pierce N W, et al. (2013) Cand1 promotes assembly of new SCF complexes through dynamic exchange of F box proteins. *Cell* 153(1):206-215.

Schulman B A, et al. (2000) Insights into SCF ubiquitin ligases from the structure of the Skp1-Skp2 complex. *Nature* 408(6810):381-386.

Sidhu S S, Lowman H B, Cunningham B C, & Wells J A (2000) Phage display for selection of novel binding peptides. *Methods in enzymology* 328:333-363.

Suzuki H, et al. (2000) Homodimer of two F-box proteins betaTrCP1 or betaTrCP2 binds to IkappaBalpha for signal-dependent ubiquitination. *The Journal of biological chemistry* 275(4):2877-2884.

Wang Z, Liu P, Inuzuka H, & Wei W (2014) Roles of F-box proteins in cancer. *Nature reviews. Cancer* 14(4):233-247.

Weathington N M & Mallampalli R K (2014) Emerging therapies targeting the ubiquitin proteasome system in cancer. *The Journal of clinical investigation* 124(1):6-12.

Welcker M, et al. (2013) Fbw7 dimerization determines the specificity and robustness of substrate degradation. *Genes & development* 27(23):2531-2536.

Wu X Z, et al. (2015) MiR-27a-3p promotes esophageal cancer cell proliferation via F-box and WD repeat domain-containing 7 (FBXW7) suppression. *International journal of clinical and experimental medicine* 8(9): 15556-15562.

Zheng N, et al. (2002) Structure of the Cul1-Rbx1-Skp1-F boxSkp2 SCF ubiquitin ligase complex. *Nature* 416 (6882):703-709.

What is claimed is:

1. A Ubv polypeptide comprising one or more amino acid substitution selected from the group consisting of A12G, I42R or V, L49R, H62Q, R63K, and G75R in the amino acid sequence of Fw7.1, and wherein amino acids 77 and 78 are optional.

2. The Ubv polypeptide of claim 1, comprising the following substitutions: A12G, I42V, L49R, H62Q, R63K, I72V, R74G, G75R, and G76R (Fw7.5), and wherein amino acids 77 and 78 are optional.

3. The Ubv polypeptide of claim 1, comprising the following substitutions:
   (a) A12G, L49R, H62Q, R63K, R74P, and G75S (Fw7.6);
   (b) A12G, I42R, S46A, R47G, K48R, L49R, H62Q, R63K, L71Y, I72V, and G75R (Fw7.7);
   (c) I42R, S46A, R47G, H62Q, R63K, L71W, I72F, F73L, G75F, and G76V (Fw7.8);
   (d) A12G, L49R, H62Q, R63K, L71M, I72V, R74S, and G75K (Fw7.9);
   (e) A9T, A12G, I42V, I44L, L49R, H62Q, R63K, L71W, I72L, F73L, and G75R (Fw7.10);
   (f) E36G, I42V, R47K, L49R, H62Q, R63K, and G75R (Fw7.11);
   (g) I42R, S46A, R47G, L49R, H62Q, R63K, I72L, G75R, and G76E (Fw7.12);
   (h) A9S, A12G, E36G, I44L, L49R, H62Q, R63K, R74S, and G76A (Fw7.13);
   (i) E36D, I42V, I44L, S46R, L49K, H62Q, R63K, V70L, L71W, F73V, and G75R (Fw7.14);
   (j) A12G, R47H, K48M, L49R, H62Q, R63K, and R74S (Fw.7.15);
   (k) A12G, E36G, I44L, L49P, H62Q, R63K, L71V, I72V, and G75R (Fw7.16);
   (l) A12G, E36G, I42R, S46A, R47G, L49R, H62Q, R63K, and T66S (Fw7.17); or
   (m) I42R, L49R, H62Q, R63K, I72L, and R74P (Fw7.18); wherein amino acids 77 and 78 are optional.

4. A Ubv polypeptide comprising the amino acid sequence of Fw11.1 (SEQ ID NO:20), wherein the sequence of Fw11.1 optionally has 1-5 substitutions.

5. The Ubv polypeptide of claim 4, comprising the following substitutions:
   (a) S12Y, S14T, and N17H (Fw11.2; SEQ ID NO:21);
   (b) S14T and Y15F (Fw11.3; SEQ ID NO:22);
   (c) S12Y (Fw11.4; SEQ ID NO:23);
   (d) S14T (Fw11.5; SEQ ID NO:24);
   (e) S14T, Y15F, and N17D (Fw11.6; SEQ ID NO:25);
   (f) S14T and N17H (Fw11.7; SEQ ID NO:26);
   (g) S12Y and S14T (Fw11.8; SEQ ID NO:27);
   (h) Y15F (Fw11.9; SEQ ID NO:28);
   (i) N17H (Fw11.10; SEQ ID NO:29);
   (j) S14N and Y15F (Fw11.11; SEQ ID NO:30);
   (k) N17D (Fw11.12; SEQ ID NO:31);
   (l) S12H and N17Y (Fw11.13; SEQ ID NO:32);
   (m) S12Y and S15F (Fw11.14; SEQ ID NO:33);
   (n) K11R and S14T (Fw11.15; SEQ ID NO:34);
   (o) S12T (Fw11.16; SEQ ID NO:35); or
   (p) S12A (Fw11.17; SEQ ID NO:36).

6. A UbV polypeptide comprising a sequence selected from the group consisting of SEQ ID NOs:2-36, or a variant thereof comprising a sequence that is at least 90% identical to a sequence selected from the group consisting of SEQ ID NOs:2-36, or a fragment thereof.

7. A nucleic acid molecule encoding a Ubv polypeptide of claim 1.

8. A nucleic acid molecule encoding a Ubv polypeptide of claim 4.

9. A nucleic acid molecule encoding a Ubv polypeptide of claim 6.

* * * * *

SEQUENCE LISTING

```
<160> NUMBER OF SEQ ID NOS: 170

<210> SEQ ID NO 1
<211> LENGTH: 78
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (77)..(77)
<223> OTHER INFORMATION: Xaa is Gly or absent
<220> FEATURE:
<221> NAME/KEY: MISC_FEATURE
<222> LOCATION: (78)..(78)
<223> OTHER INFORMATION: Xaa is Gly or absent

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Xaa Xaa
65                  70                  75

<210> SEQ ID NO 2
<211> LENGTH: 78
<212> TYPE: PRT
<213> ORGANISM: Artificial Sequence
<220> FEATURE:
<223> OTHER INFORMATION: Synthetic Construct

<400> SEQUENCE: 2

Met Gln Ile Phe Val Lys Thr Gly Ala Arg Thr Ala Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Ile Phe Ser Arg Lys
        35                  40                  45

Leu Leu Glu Asp Gly Arg Thr Leu Ser Asp Tyr Asn Ile His Arg Glu
    50                  55                  60
```

```
Ser Thr Leu Arg Leu Val Leu Ile Phe Arg Gly Asn Glu Ser
 65                  70                  75
```

<210> SEQ ID NO 3
<211> LENGTH: 78
<212> TYPE: PRT
<213> ORGANISM: Artificial Sequence
<220> FEATURE:
<223> OTHER INFORMATION: Synthetic Construct

<400> SEQUENCE: 3

```
Met Gln Ile Phe Val Lys Thr Gly Thr Val Thr Asn Ile Ile Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Thr Leu Ile Phe Ala Gly Lys
         35                  40                  45

Gln Leu Glu Asp Gly Arg Thr Leu Ser Asp Tyr Asn Ile Glu Lys Glu
     50                  55                  60

Ser Ser Leu Arg Leu Val Leu Arg Phe Gly Gly Leu Thr Ala
 65                  70                  75
```

<210> SEQ ID NO 4
<211> LENGTH: 78
<212> TYPE: PRT
<213> ORGANISM: Artificial Sequence
<220> FEATURE:
<223> OTHER INFORMATION: Synthetic Construct

<400> SEQUENCE: 4

```
Met His Ile Leu Val Lys Thr Gly Thr Val Thr Thr Ile Thr Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Ile Leu Val Phe Tyr Gly Lys
         35                  40                  45

Gln Leu Glu Asp Gly Arg Thr Leu Ser Asp Tyr Asn Ile Gln Lys Glu
     50                  55                  60

Ser Thr Leu Gln Leu Leu Arg Phe Leu Gly Gly Arg Pro
 65                  70                  75
```

<210> SEQ ID NO 5
<211> LENGTH: 78
<212> TYPE: PRT
<213> ORGANISM: Artificial Sequence
<220> FEATURE:
<223> OTHER INFORMATION: Synthetic Construct

<400> SEQUENCE: 5

```
Met Gln Ile Phe Val Lys Thr Gly Ala Gly Thr Asn Ile Thr Leu Glu
  1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Ile Leu Ile Phe Ser Gly Lys
         35                  40                  45

Leu Leu Glu Asp Gly Arg Thr Leu Ser Asp Tyr Asn Ile His Arg Glu
     50                  55                  60

Ser Thr Leu Arg Leu Val Leu Ile Phe Arg Gly Asn Glu Ala
 65                  70                  75
```

```
<210> SEQ ID NO 6
<211> LENGTH: 76
<212> TYPE: PRT
<213> ORGANISM: Artificial Sequence
<220> FEATURE:
<223> OTHER INFORMATION: Synthetic Construct

<400> SEQUENCE: 6

Met Gln Ile Phe Val Lys Thr Gly Ala Arg Thr Gly Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Val Leu Ile Phe Ser Arg Lys
        35                  40                  45

Arg Leu Glu Asp Gly Arg Thr Leu Ser Asp Tyr Asn Ile Gln Lys Glu
    50                  55                  60

Ser Thr Leu Arg Leu Val Leu Val Phe Gly Arg Arg
65                  70                  75

<210> SEQ ID NO 7
<211> LENGTH: 76
<212> TYPE: PRT
<213> ORGANISM: Artificial Sequence
<220> FEATURE:
<223> OTHER INFORMATION: Synthetic Construct

<400> SEQUENCE: 7

Met Gln Ile Phe Val Lys Thr Gly Ala Arg Thr Gly Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Ile Phe Ser Arg Lys
        35                  40                  45

Arg Leu Glu Asp Gly Arg Thr Leu Ser Asp Tyr Asn Ile Gln Lys Glu
    50                  55                  60

Ser Thr Leu Arg Leu Val Leu Ile Phe Pro Ser Gly
65                  70                  75

<210> SEQ ID NO 8
<211> LENGTH: 76
<212> TYPE: PRT
<213> ORGANISM: Artificial Sequence
<220> FEATURE:
<223> OTHER INFORMATION: Synthetic Construct

<400> SEQUENCE: 8

Met Gln Ile Phe Val Lys Thr Gly Ala Arg Thr Gly Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Arg
        35                  40                  45

Arg Leu Glu Asp Gly Arg Thr Leu Ser Asp Tyr Asn Ile Gln Lys Glu
    50                  55                  60

Ser Thr Leu Arg Leu Val Tyr Val Phe Arg Arg Gly
65                  70                  75

<210> SEQ ID NO 9
<211> LENGTH: 76
<212> TYPE: PRT
<213> ORGANISM: Artificial Sequence
```

```
<220> FEATURE:
<223> OTHER INFORMATION: Synthetic Construct

<400> SEQUENCE: 9

Met Gln Ile Phe Val Lys Thr Gly Ala Arg Thr Ala Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Leu Leu Glu Asp Gly Arg Thr Leu Ser Asp Tyr Asn Ile Gln Lys Glu
    50                  55                  60

Ser Thr Leu Arg Leu Val Trp Phe Leu Arg Phe Val
65                  70                  75

<210> SEQ ID NO 10
<211> LENGTH: 76
<212> TYPE: PRT
<213> ORGANISM: Artificial Sequence
<220> FEATURE:
<223> OTHER INFORMATION: Synthetic Construct

<400> SEQUENCE: 10

Met Gln Ile Phe Val Lys Thr Gly Ala Arg Thr Gly Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Ile Phe Ser Arg Lys
        35                  40                  45

Arg Leu Glu Asp Gly Arg Thr Leu Ser Asp Tyr Asn Ile Gln Lys Glu
    50                  55                  60

Ser Thr Leu Arg Leu Val Met Val Phe Ser Lys Gly
65                  70                  75

<210> SEQ ID NO 11
<211> LENGTH: 76
<212> TYPE: PRT
<213> ORGANISM: Artificial Sequence
<220> FEATURE:
<223> OTHER INFORMATION: Synthetic Construct

<400> SEQUENCE: 11

Met Gln Ile Phe Val Lys Thr Gly Thr Arg Thr Gly Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Val Leu Leu Phe Ser Arg Lys
        35                  40                  45

Val Leu Glu Asp Gly Arg Thr Leu Ser Asp Tyr Asn Ile Gln Lys Glu
    50                  55                  60

Ser Thr Leu Arg Leu Val Trp Leu Leu Arg Arg Gly
65                  70                  75

<210> SEQ ID NO 12
<211> LENGTH: 76
<212> TYPE: PRT
<213> ORGANISM: Artificial Sequence
<220> FEATURE:
<223> OTHER INFORMATION: Synthetic Construct

<400> SEQUENCE: 12
```

Met Gln Ile Phe Val Lys Thr Gly Ala Arg Thr Ala Ile Thr Leu Glu
1               5                   10                  15

Val Glu Pro Ser Asp Thr Ile Glu Asn Val Lys Ala Lys Ile Gln Asp
                20                  25                  30

Lys Gly Gly Ile Pro Pro Asp Gln Gln Val Leu Ile Phe Ser Lys Lys
            35                  40                  45

Arg Leu Glu Asp Gly Arg Thr Leu Ser Asp Tyr Asn Ile Gln Lys Glu
        50                  55                  60

Ser Thr Leu Arg Leu Val Leu Ile Phe Arg Arg Gly
65                  70                  75

<210> SEQ ID NO 13
<211> LENGTH: 76
<212> TYPE: PRT
<213> ORGANISM: Artificial Sequence
<220> FEATURE:
<223> OTHER INFORMATION: Synthetic Construct

<400> SEQUENCE: 13

Met Gln Ile Phe Val Lys Thr Gly Ala Arg Thr Ala Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Arg Leu Glu Asp Gly Arg Thr Leu Ser Asp Tyr Asn Ile Gln Lys Glu
        50                  55                  60

Ser Thr Leu Arg Leu Val Leu Leu Phe Arg Arg Glu
65                  70                  75

<210> SEQ ID NO 14
<211> LENGTH: 76
<212> TYPE: PRT
<213> ORGANISM: Artificial Sequence
<220> FEATURE:
<223> OTHER INFORMATION: Synthetic Construct

<400> SEQUENCE: 14

Met Gln Ile Phe Val Lys Thr Gly Ser Arg Thr Gly Ile Thr Leu Glu
1               5                   10                  15

Val Glu Pro Ser Asp Thr Ile Glu Asn Val Lys Ala Lys Ile Gln Asp
                20                  25                  30

Lys Gly Gly Ile Pro Pro Asp Gln Gln Ile Leu Leu Phe Ser Arg Lys
            35                  40                  45

Arg Leu Glu Asp Gly Arg Thr Leu Ser Asp Tyr Asn Ile Gln Lys Glu
        50                  55                  60

Ser Thr Leu Arg Leu Val Leu Ile Phe Ser Gly Ala
65                  70                  75

<210> SEQ ID NO 15
<211> LENGTH: 76
<212> TYPE: PRT
<213> ORGANISM: Artificial Sequence
<220> FEATURE:
<223> OTHER INFORMATION: Synthetic Construct

<400> SEQUENCE: 15

Met Gln Ile Phe Val Lys Thr Gly Ala Arg Thr Ala Ile Thr Leu Glu
1               5                   10                  15

Val Glu Pro Ser Asp Thr Ile Glu Asn Val Lys Ala Lys Ile Gln Asp
            20                  25                  30

Lys Asp Gly Ile Pro Pro Asp Gln Gln Val Leu Leu Phe Arg Arg Lys
        35                  40                  45

Lys Leu Glu Asp Gly Arg Thr Leu Ser Asp Tyr Asn Ile Gln Lys Glu
    50                  55                  60

Ser Thr Leu Arg Leu Leu Trp Ile Val Arg Arg Gly
65                  70                  75

<210> SEQ ID NO 16
<211> LENGTH: 76
<212> TYPE: PRT
<213> ORGANISM: Artificial Sequence
<220> FEATURE:
<223> OTHER INFORMATION: Synthetic Construct

<400> SEQUENCE: 16

Met Gln Ile Phe Val Lys Thr Gly Ala Arg Thr Gly Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Ile Leu Ile Phe Ser His Met
        35                  40                  45

Arg Leu Glu Asp Gly Arg Thr Leu Ser Asp Tyr Asn Ile Gln Lys Glu
    50                  55                  60

Ser Thr Leu Arg Leu Val Leu Ile Phe Ser Gly Gly
65                  70                  75

<210> SEQ ID NO 17
<211> LENGTH: 76
<212> TYPE: PRT
<213> ORGANISM: Artificial Sequence
<220> FEATURE:
<223> OTHER INFORMATION: Synthetic Construct

<400> SEQUENCE: 17

Met Gln Ile Phe Val Lys Thr Gly Ala Arg Thr Gly Ile Thr Leu Glu
1               5                   10                  15

Val Glu Pro Ser Asp Thr Ile Glu Asn Val Lys Ala Lys Ile Gln Asp
            20                  25                  30

Lys Gly Gly Ile Pro Pro Asp Gln Gln Ile Leu Leu Phe Ser Arg Lys
        35                  40                  45

Pro Leu Glu Asp Gly Arg Thr Leu Ser Asp Tyr Asn Ile Gln Lys Glu
    50                  55                  60

Ser Thr Leu Arg Leu Val Val Val Phe Arg Arg Gly
65                  70                  75

<210> SEQ ID NO 18
<211> LENGTH: 76
<212> TYPE: PRT
<213> ORGANISM: Artificial Sequence
<220> FEATURE:
<223> OTHER INFORMATION: Synthetic Construct

<400> SEQUENCE: 18

Met Gln Ile Phe Val Lys Thr Gly Ala Arg Thr Gly Ile Thr Leu Glu
1               5                   10                  15

Val Glu Pro Ser Asp Thr Ile Glu Asn Val Lys Ala Lys Ile Gln Asp
            20                  25                  30

Lys Gly Gly Ile Pro Pro Asp Gln Gln Arg Leu Ile Phe Ala Gly Lys

```
                35                  40                  45
Arg Leu Glu Asp Gly Arg Thr Leu Ser Asp Tyr Asn Ile Gln Lys Glu
 50                  55                  60

Ser Ser Leu Arg Leu Val Leu Ile Phe Arg Gly Gly
 65                  70                  75

<210> SEQ ID NO 19
<211> LENGTH: 76
<212> TYPE: PRT
<213> ORGANISM: Artificial Sequence
<220> FEATURE:
<223> OTHER INFORMATION: Synthetic Construct

<400> SEQUENCE: 19

Met Gln Ile Phe Val Lys Thr Gly Ala Arg Thr Ala Ile Thr Leu Glu
 1               5                  10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ser Arg Lys
             35                  40                  45

Arg Leu Glu Asp Gly Arg Thr Leu Ser Asp Tyr Asn Ile Gln Lys Glu
 50                  55                  60

Ser Thr Leu Arg Leu Val Leu Leu Phe Pro Gly Gly
 65                  70                  75

<210> SEQ ID NO 20
<211> LENGTH: 84
<212> TYPE: PRT
<213> ORGANISM: Artificial Sequence
<220> FEATURE:
<223> OTHER INFORMATION: Synthetic Construct

<400> SEQUENCE: 20

Met Gln Ile Phe Val Lys Thr Tyr Pro Tyr Lys Ser Gly Ser Tyr His
 1               5                  10                  15

Asn Asn Tyr Thr Ile Thr Leu Glu Val Glu Pro Ser Asp Thr Ile Glu
                20                  25                  30

Asn Val Lys Ala Lys Ile Gln Asp Lys Glu Gly Ile Pro Pro Asp Gln
             35                  40                  45

Gln Val Leu Ile Phe Ser Arg Lys Arg Leu Glu Asp Gly Arg Thr Leu
     50                  55                  60

Ser Asp Tyr Asn Ile Gln Lys Glu Ser Thr Leu Arg Leu Val Leu Val
 65                  70                  75                  80

Phe Gly Arg Arg

<210> SEQ ID NO 21
<211> LENGTH: 84
<212> TYPE: PRT
<213> ORGANISM: Artificial Sequence
<220> FEATURE:
<223> OTHER INFORMATION: Synthetic Construct

<400> SEQUENCE: 21

Met Gln Ile Phe Val Lys Thr Tyr Pro Tyr Lys Tyr Gly Thr Tyr His
 1               5                  10                  15

His Asn Tyr Thr Ile Thr Leu Glu Val Glu Pro Ser Asp Thr Ile Glu
                20                  25                  30

Asn Val Lys Ala Lys Ile Gln Asp Lys Glu Gly Ile Pro Pro Asp Gln
             35                  40                  45
```

```
Gln Val Leu Ile Phe Ser Arg Lys Arg Leu Glu Asp Gly Arg Thr Leu
    50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 22
<211> LENGTH: 84
<212> TYPE: PRT
<213> ORGANISM: Artificial Sequence
<220> FEATURE:
<223> OTHER INFORMATION: Synthetic Construct

<400> SEQUENCE: 22

Met Gln Ile Phe Val Lys Thr Tyr Pro Tyr Lys Ser Gly Thr Phe His
1               5                   10                  15

Asn Asn Tyr Thr Ile Thr Leu Glu Val Glu Pro Ser Asp Thr Ile Glu
                20                  25                  30

Asn Val Lys Ala Lys Ile Gln Asp Lys Glu Gly Ile Pro Pro Asp Gln
            35                  40                  45

Gln Val Leu Ile Phe Ser Arg Lys Arg Leu Glu Asp Gly Arg Thr Leu
        50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 23
<211> LENGTH: 84
<212> TYPE: PRT
<213> ORGANISM: Artificial Sequence
<220> FEATURE:
<223> OTHER INFORMATION: Synthetic Construct

<400> SEQUENCE: 23

Met Gln Ile Phe Val Lys Thr Tyr Pro Tyr Lys Tyr Gly Ser Tyr His
1               5                   10                  15

Asn Asn Tyr Thr Ile Thr Leu Glu Val Glu Pro Ser Asp Thr Ile Glu
                20                  25                  30

Asn Val Lys Ala Lys Ile Gln Asp Lys Glu Gly Ile Pro Pro Asp Gln
            35                  40                  45

Gln Val Leu Ile Phe Ser Arg Lys Arg Leu Glu Asp Gly Arg Thr Leu
        50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 24
<211> LENGTH: 84
<212> TYPE: PRT
<213> ORGANISM: Artificial Sequence
<220> FEATURE:
<223> OTHER INFORMATION: Synthetic Construct

<400> SEQUENCE: 24

Met Gln Ile Phe Val Lys Thr Tyr Pro Tyr Lys Ser Gly Thr Tyr His
1               5                   10                  15

Asn Asn Tyr Thr Ile Thr Leu Glu Val Glu Pro Ser Asp Thr Ile Glu
                20                  25                  30

Asn Val Lys Ala Lys Ile Gln Asp Lys Glu Gly Ile Pro Pro Asp Gln
```

```
            35                  40                  45

Gln Val Leu Ile Phe Ser Arg Lys Arg Leu Glu Asp Gly Arg Thr Leu
    50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 25
<211> LENGTH: 84
<212> TYPE: PRT
<213> ORGANISM: Artificial Sequence
<220> FEATURE:
<223> OTHER INFORMATION: Synthetic Construct

<400> SEQUENCE: 25

Met Gln Ile Phe Val Lys Thr Tyr Pro Tyr Lys Ser Gly Thr Phe His
1               5                   10                  15

Asp Asn Tyr Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
        35                  40                  45

Gln Val Leu Ile Phe Ser Arg Lys Arg Leu Glu Asp Gly Arg Thr Leu
    50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 26
<211> LENGTH: 84
<212> TYPE: PRT
<213> ORGANISM: Artificial Sequence
<220> FEATURE:
<223> OTHER INFORMATION: Synthetic Construct

<400> SEQUENCE: 26

Met Gln Ile Phe Val Lys Thr Tyr Pro Tyr Lys Ser Gly Thr Tyr His
1               5                   10                  15

His Asn Tyr Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
        35                  40                  45

Gln Val Leu Ile Phe Ser Arg Lys Arg Leu Glu Asp Gly Arg Thr Leu
    50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 27
<211> LENGTH: 84
<212> TYPE: PRT
<213> ORGANISM: Artificial Sequence
<220> FEATURE:
<223> OTHER INFORMATION: Synthetic Construct

<400> SEQUENCE: 27

Met Gln Ile Phe Val Lys Thr Tyr Pro Tyr Lys Tyr Gly Thr Tyr His
1               5                   10                  15

Asn Asn Tyr Thr Ile Thr Leu Glu Val Glu Pro Ser Asp Thr Ile Glu
            20                  25                  30
```

```
Asn Val Lys Ala Lys Ile Gln Asp Lys Glu Gly Ile Pro Pro Asp Gln
            35                  40                  45

Gln Val Leu Ile Phe Ser Arg Lys Arg Leu Glu Asp Gly Arg Thr Leu
 50                  55                  60

Ser Asp Tyr Asn Ile Gln Lys Glu Ser Thr Leu Arg Leu Val Leu Val
 65                  70                  75                  80

Phe Gly Arg Arg
```

<210> SEQ ID NO 28
<211> LENGTH: 84
<212> TYPE: PRT
<213> ORGANISM: Artificial Sequence
<220> FEATURE:
<223> OTHER INFORMATION: Synthetic Construct

<400> SEQUENCE: 28

```
Met Gln Ile Phe Val Lys Thr Tyr Pro Tyr Lys Ser Gly Ser Phe His
 1               5                  10                  15

Asn Asn Tyr Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
            35                  40                  45

Gln Val Leu Ile Phe Ser Arg Lys Arg Leu Glu Asp Gly Arg Thr Leu
 50                  55                  60

Ser Asp Tyr Asn Ile Gln Lys Glu Ser Thr Leu Arg Leu Val Leu Val
 65                  70                  75                  80

Phe Gly Arg Arg
```

<210> SEQ ID NO 29
<211> LENGTH: 84
<212> TYPE: PRT
<213> ORGANISM: Artificial Sequence
<220> FEATURE:
<223> OTHER INFORMATION: Synthetic Construct

<400> SEQUENCE: 29

```
Met Gln Ile Phe Val Lys Thr Tyr Pro Tyr Lys Ser Gly Ser Tyr His
 1               5                  10                  15

His Asn Tyr Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
            35                  40                  45

Gln Val Leu Ile Phe Ser Arg Lys Arg Leu Glu Asp Gly Arg Thr Leu
 50                  55                  60

Ser Asp Tyr Asn Ile Gln Lys Glu Ser Thr Leu Arg Leu Val Leu Val
 65                  70                  75                  80

Phe Gly Arg Arg
```

<210> SEQ ID NO 30
<211> LENGTH: 84
<212> TYPE: PRT
<213> ORGANISM: Artificial Sequence
<220> FEATURE:
<223> OTHER INFORMATION: Synthetic Construct

<400> SEQUENCE: 30

```
Met Gln Ile Phe Val Lys Thr Tyr Pro Tyr Lys Ser Gly Asn Phe His
 1               5                  10                  15
```

Asn Asn Tyr Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
        35                  40                  45

Gln Val Leu Ile Phe Ser Arg Lys Arg Leu Glu Asp Gly Arg Thr Leu
    50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 31
<211> LENGTH: 84
<212> TYPE: PRT
<213> ORGANISM: Artificial Sequence
<220> FEATURE:
<223> OTHER INFORMATION: Synthetic Construct

<400> SEQUENCE: 31

Met Gln Ile Phe Val Lys Thr Tyr Pro Tyr Lys Ser Gly Ser Tyr His
1               5                   10                  15

Asp Asn Tyr Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
        35                  40                  45

Gln Val Leu Ile Phe Ser Arg Lys Arg Leu Glu Asp Gly Arg Thr Leu
    50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 32
<211> LENGTH: 84
<212> TYPE: PRT
<213> ORGANISM: Artificial Sequence
<220> FEATURE:
<223> OTHER INFORMATION: Synthetic Construct

<400> SEQUENCE: 32

Met Gln Ile Phe Val Lys Thr Tyr Pro Tyr Lys His Gly Ser Tyr His
1               5                   10                  15

Tyr Asn Tyr Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
        35                  40                  45

Gln Val Leu Ile Phe Ser Arg Lys Arg Leu Glu Asp Gly Arg Thr Leu
    50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 33
<211> LENGTH: 84
<212> TYPE: PRT
<213> ORGANISM: Artificial Sequence
<220> FEATURE:
<223> OTHER INFORMATION: Synthetic Construct

<400> SEQUENCE: 33

Met Gln Ile Phe Val Lys Thr Tyr Pro Tyr Lys Tyr Gly Ser Phe His

```
                1               5                  10                 15
Asn Asn Tyr Thr Ile Thr Leu Glu Val Glu Pro Ser Asp Thr Ile Glu
                20                 25                 30

Asn Val Lys Ala Lys Ile Gln Asp Lys Glu Gly Ile Pro Pro Asp Gln
            35                 40                 45

Gln Val Leu Ile Phe Ser Arg Lys Arg Leu Glu Asp Gly Arg Thr Leu
        50                 55                 60

Ser Asp Tyr Asn Ile Gln Lys Glu Ser Thr Leu Arg Leu Val Leu Val
65                 70                 75                 80

Phe Gly Arg Arg

<210> SEQ ID NO 34
<211> LENGTH: 84
<212> TYPE: PRT
<213> ORGANISM: Artificial Sequence
<220> FEATURE:
<223> OTHER INFORMATION: Synthetic Construct

<400> SEQUENCE: 34

Met Gln Ile Phe Val Lys Thr Tyr Pro Tyr Arg Ser Gly Thr Tyr His
1               5                  10                 15

Asn Asn Tyr Thr Ile Thr Leu Glu Val Glu Pro Ser Asp Thr Ile Glu
                20                 25                 30

Asn Val Lys Ala Lys Ile Gln Asp Lys Glu Gly Ile Pro Pro Asp Gln
            35                 40                 45

Gln Val Leu Ile Phe Ser Arg Lys Arg Leu Glu Asp Gly Arg Thr Leu
        50                 55                 60

Ser Asp Tyr Asn Ile Gln Lys Glu Ser Thr Leu Arg Leu Val Leu Val
65                 70                 75                 80

Phe Gly Arg Arg

<210> SEQ ID NO 35
<211> LENGTH: 84
<212> TYPE: PRT
<213> ORGANISM: Artificial Sequence
<220> FEATURE:
<223> OTHER INFORMATION: Synthetic Construct

<400> SEQUENCE: 35

Met Gln Ile Phe Val Lys Thr Tyr Pro Tyr Lys Thr Gly Ser Tyr His
1               5                  10                 15

Asn Asn Tyr Thr Ile Thr Leu Glu Val Glu Pro Ser Asp Thr Ile Glu
                20                 25                 30

Asn Val Lys Ala Lys Ile Gln Asp Lys Glu Gly Ile Pro Pro Asp Gln
            35                 40                 45

Gln Val Leu Ile Phe Ser Arg Lys Arg Leu Glu Asp Gly Arg Thr Leu
        50                 55                 60

Ser Asp Tyr Asn Ile Gln Lys Glu Ser Thr Leu Arg Leu Val Leu Val
65                 70                 75                 80

Phe Gly Arg Arg

<210> SEQ ID NO 36
<211> LENGTH: 84
<212> TYPE: PRT
<213> ORGANISM: Artificial Sequence
<220> FEATURE:
<223> OTHER INFORMATION: Synthetic Construct

<400> SEQUENCE: 36
```

```
Met Gln Ile Phe Val Lys Thr Tyr Pro Tyr Lys Ala Gly Ser Tyr His
1               5                   10                  15

Asn Asn Tyr Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
        35                  40                  45

Gln Val Leu Ile Phe Ser Arg Lys Arg Leu Glu Asp Gly Arg Thr Leu
    50                  55                  60

Ser Asp Tyr Asn Ile Gln Lys Glu Ser Thr Leu Arg Leu Val Leu Val
65                  70                  75                  80

Phe Gly Arg Arg

<210> SEQ ID NO 37
<211> LENGTH: 78
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is His or Gln
<220> FEATURE:
<221> NAME/KEY: MISC_FEATURE
<222> LOCATION: (4)..(4)
<223> OTHER INFORMATION: Xaa is Phe or Leu
<220> FEATURE:
<221> NAME/KEY: MISC_FEATURE
<222> LOCATION: (8)..(8)
<223> OTHER INFORMATION: Xaa is Gly or Leu
<220> FEATURE:
<221> NAME/KEY: MISC_FEATURE
<222> LOCATION: (9)..(9)
<223> OTHER INFORMATION: Xaa is Ala, Ser, or Thr
<220> FEATURE:
<221> NAME/KEY: MISC_FEATURE
<222> LOCATION: (10)..(10)
<223> OTHER INFORMATION: Xaa is Gly, Arg, or Val
<220> FEATURE:
<221> NAME/KEY: MISC_FEATURE
<222> LOCATION: (11)..(11)
<223> OTHER INFORMATION: Xaa is Lys or Thr
<220> FEATURE:
<221> NAME/KEY: MISC_FEATURE
<222> LOCATION: (12)..(12)
<223> OTHER INFORMATION: Xaa is Ala, Gly, Asn, or Thr
<220> FEATURE:
<221> NAME/KEY: MISC_FEATURE
<222> LOCATION: (14)..(14)
<223> OTHER INFORMATION: Xaa is Ile or Thr
<220> FEATURE:
<221> NAME/KEY: MISC_FEATURE
<222> LOCATION: (42)..(42)
<223> OTHER INFORMATION: Xaa is Ile, Arg, Thr, or Val
<220> FEATURE:
<221> NAME/KEY: MISC_FEATURE
<222> LOCATION: (44)..(44)
<223> OTHER INFORMATION: Xaa is Ile, Leu, or Val
<220> FEATURE:
<221> NAME/KEY: MISC_FEATURE
<222> LOCATION: (46)..(46)
<223> OTHER INFORMATION: Xaa is Ala, Arg, Ser, or Tyr
<220> FEATURE:
<221> NAME/KEY: MISC_FEATURE
<222> LOCATION: (47)..(47)
<223> OTHER INFORMATION: Xaa is Gly, His, Lys, or Arg
<220> FEATURE:
<221> NAME/KEY: MISC_FEATURE
<222> LOCATION: (48)..(48)
<223> OTHER INFORMATION: Xaa is Lys, Met, or Arg
<220> FEATURE:
<221> NAME/KEY: MISC_FEATURE
```

```
<222> LOCATION: (49)..(49)
<223> OTHER INFORMATION: Xaa is Lys, Leu, Pro, Gln, Arg, or Val
<220> FEATURE:
<221> NAME/KEY: MISC_FEATURE
<222> LOCATION: (62)..(62)
<223> OTHER INFORMATION: Xaa is Glu, His, or Gln
<220> FEATURE:
<221> NAME/KEY: MISC_FEATURE
<222> LOCATION: (63)..(63)
<223> OTHER INFORMATION: Xaa is Lys or Arg
<220> FEATURE:
<221> NAME/KEY: MISC_FEATURE
<222> LOCATION: (66)..(66)
<223> OTHER INFORMATION: Xaa is Ser or Thr
<220> FEATURE:
<221> NAME/KEY: MISC_FEATURE
<222> LOCATION: (68)..(68)
<223> OTHER INFORMATION: Xaa is His, Gln, or Arg
<220> FEATURE:
<221> NAME/KEY: MISC_FEATURE
<222> LOCATION: (70)..(70)
<223> OTHER INFORMATION: Xaa is Leu or Val
<220> FEATURE:
<221> NAME/KEY: MISC_FEATURE
<222> LOCATION: (71)..(71)
<223> OTHER INFORMATION: Xaa is Leu, Met, Val, Trp, or Tyr
<220> FEATURE:
<221> NAME/KEY: MISC_FEATURE
<222> LOCATION: (72)..(72)
<223> OTHER INFORMATION: Xaa is Phe, Ile, Leu, Arg, or Val
<220> FEATURE:
<221> NAME/KEY: MISC_FEATURE
<222> LOCATION: (73)..(73)
<223> OTHER INFORMATION: Xaa is Phe, Leu, or Val
<220> FEATURE:
<221> NAME/KEY: MISC_FEATURE
<222> LOCATION: (74)..(74)
<223> OTHER INFORMATION: Xaa is Gly, Leu, Pro, Arg, or Ser
<220> FEATURE:
<221> NAME/KEY: MISC_FEATURE
<222> LOCATION: (75)..(75)
<223> OTHER INFORMATION: Xaa is Phe, Gly, Lys, Arg, or Ser
<220> FEATURE:
<221> NAME/KEY: MISC_FEATURE
<222> LOCATION: (76)..(76)
<223> OTHER INFORMATION: Xaa is Ala, Glu, Gly, Leu, Asn, Arg, or Val
<220> FEATURE:
<221> NAME/KEY: MISC_FEATURE
<222> LOCATION: (77)..(77)
<223> OTHER INFORMATION: Xaa is Glu, Gly, Arg, Thr, or absent
<220> FEATURE:
<221> NAME/KEY: MISC_FEATURE
<222> LOCATION: (78)..(78)
<223> OTHER INFORMATION: Xaa is Ala, Gly, Pro, Ser, or absent

<400> SEQUENCE: 37

Met Xaa Ile Xaa Val Lys Thr Xaa Xaa Xaa Xaa Xaa Ile Xaa Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Xaa Leu Xaa Phe Xaa Xaa Xaa
        35                  40                  45

Xaa Leu Glu Asp Gly Arg Thr Leu Ser Asp Tyr Asn Ile Xaa Xaa Glu
    50                  55                  60

Ser Xaa Leu Xaa Leu Xaa Xaa Xaa Xaa Xaa Xaa Xaa Xaa Xaa
65                  70                  75

<210> SEQ ID NO 38
<211> LENGTH: 33
<212> TYPE: PRT
<213> ORGANISM: Artificial Sequence
<220> FEATURE:
<223> OTHER INFORMATION: Synthetic Construct
```

<400> SEQUENCE: 38

Arg Met Lys Gln Leu Glu Asp Lys Ile Glu Glu Leu Leu Ser Lys Ile
1               5                   10                  15

Tyr His Leu Glu Asn Glu Ile Ala Arg Leu Lys Lys Leu Ile Gly Glu
            20                  25                  30

Arg

<210> SEQ ID NO 39
<211> LENGTH: 21
<212> TYPE: DNA
<213> ORGANISM: Artificial Sequence
<220> FEATURE:
<223> OTHER INFORMATION: Synthetic Construct

<400> SEQUENCE: 39
cggaagaguu uuucgacuat t                                              21

<210> SEQ ID NO 40
<211> LENGTH: 21
<212> TYPE: DNA
<213> ORGANISM: Artificial Sequence
<220> FEATURE:
<223> OTHER INFORMATION: Synthetic Construct

<400> SEQUENCE: 40
gguuguuagu ggaucaucat t                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic Construct

<400> SEQUENCE: 41
cgggugaauu uauucgaaat t                                              21

<210> SEQ ID NO 42
<211> LENGTH: 25
<212> TYPE: PRT
<213> ORGANISM: Artificial Sequence
<220> FEATURE:
<223> OTHER INFORMATION: Synthetic Construct

<400> SEQUENCE: 42

Met Ser Tyr Tyr His His His His His His Asp Tyr Asp Ile Pro Thr
1               5                   10                  15

Thr Glu Asn Leu Tyr Phe Gln Gly Ala
            20                  25

<210> SEQ ID NO 43
<211> LENGTH: 15
<212> TYPE: PRT
<213> ORGANISM: Artificial Sequence
<220> FEATURE:
<223> OTHER INFORMATION: Synthetic Construct

<400> SEQUENCE: 43

Asp Tyr Asp Ile Pro Thr Thr Glu Asn Leu Tyr Phe Gln Gly Ala
1               5                   10                  15

<210> SEQ ID NO 44
<211> LENGTH: 31

<212> TYPE: PRT
<213> ORGANISM: Artificial Sequence
<220> FEATURE:
<223> OTHER INFORMATION: Synthetic Construct

<400> SEQUENCE: 44

Met Gly Ser Ser His His His His His His Ser Gly Arg Glu Asn
1               5                   10                  15

Leu Tyr Phe Gln Gly His Met Asp Tyr Lys Asp Asp Asp Lys
            20                  25                  30

<210> SEQ ID NO 45
<211> LENGTH: 27
<212> TYPE: PRT
<213> ORGANISM: Artificial Sequence
<220> FEATURE:
<223> OTHER INFORMATION: Synthetic Construct

<400> SEQUENCE: 45

Met Ala His His His His His His Val Thr Ser Leu Tyr Lys Lys Ala
1               5                   10                  15

Gly Glu Asn Leu Tyr Phe Gln Gly Ser Gly Ser
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthetic Construct

<400> SEQUENCE: 46

Met Ala His His His His His His Val Thr Ser Leu Tyr Lys Lys Ala
1               5                   10                  15

Gly Asp Tyr Lys Asp Asp Asp Lys
            20                  25

<210> SEQ ID NO 47
<211> LENGTH: 39
<212> TYPE: PRT
<213> ORGANISM: Artificial Sequence
<220> FEATURE:
<223> OTHER INFORMATION: Synthetic Construct

<400> SEQUENCE: 47

Met Asp Tyr Lys Asp Asp Asp Lys Gly Gln Gly Pro Asp Pro Ser Thr
1               5                   10                  15

Asn Ser Ala Asp Ile Thr Ser Leu Tyr Lys Lys Ala Gly Thr Met Asp
            20                  25                  30

Tyr Lys Asp Asp Asp Lys
        35

<210> SEQ ID NO 48
<211> LENGTH: 61
<212> TYPE: PRT
<213> ORGANISM: Artificial Sequence
<220> FEATURE:
<223> OTHER INFORMATION: Synthetic Construct

<400> SEQUENCE: 48

Met Asp Tyr Lys Asp Asp Asp Lys Gly Gln Arg Met Lys Gln Leu Glu
1               5                   10                  15

Asp Lys Ile Glu Glu Leu Leu Ser Lys Ile Tyr His Leu Glu Asn Glu
            20                  25                  30

```
Ile Ala Arg Leu Lys Lys Leu Ile Gly Glu Arg Thr Ser Leu Tyr Lys
         35                  40                  45

Lys Ala Gly Thr Met Asp Tyr Lys Asp Asp Asp Lys
         50                  55                  60

<210> SEQ ID NO 49
<211> LENGTH: 33
<212> TYPE: PRT
<213> ORGANISM: Artificial Sequence
<220> FEATURE:
<223> OTHER INFORMATION: Synthetic Construct

<400> SEQUENCE: 49

Met Tyr Pro Tyr Asp Val Pro Asp Tyr Ala Gly Gln Gly Pro Asp Pro
1               5                   10                  15

Ser Thr Asn Ser Ala Asp Ile Thr Ser Leu Tyr Lys Lys Ala Gly Ser
            20                  25                  30

Thr

<210> SEQ ID NO 50
<211> LENGTH: 31
<212> TYPE: PRT
<213> ORGANISM: Artificial Sequence
<220> FEATURE:
<223> OTHER INFORMATION: Synthetic Construct

<400> SEQUENCE: 50

Met Asp Tyr Lys Asp Asp Asp Lys Gly Gln Gly Pro Asp Pro Ser
1               5                   10                  15

Thr Asn Ser Ala Asp Ile Thr Ser Leu Tyr Lys Lys Ala Gly Thr
            20                  25                  30

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct

<400> SEQUENCE: 51

Met Asp Tyr Lys Asp Asp Asp Asp Lys
1               5

<210> SEQ ID NO 52
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t

<400> SEQUENCE: 52
atgcagattt tcgtgnnnnn nggtnnncgt accnnnatca ccctcgaggt          50
```

<210> SEQ ID NO 53
<211> LENGTH: 78
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(18)
<223> OTHER INFORMATION: n is a, c, g, or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: misc_feature
<222> LOCATION: (46)..(48)
<223> OTHER INFORMATION: n is a, c, g, or t
<220> FEATURE:
<221> NAME/KEY: misc_feature
<222> LOCATION: (52)..(63)
<223> OTHER INFORMATION: n is a, c, g, or t

<400> SEQUENCE: 53
aagatccagg ataagnnngg aattcctcct gatcagcagn nnctgnnntt tnnnnnnnnn    60
nnnctggaag atggacgt                                                 78

<210> SEQ ID NO 54
<211> LENGTH: 63
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(18)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (28)..(48)
<223> OTHER INFORMATION: n is a, c, g, or t

<400> SEQUENCE: 54
attcaaaagg agtctnnnct tnnncttnnn nnnnnnnnnn nnnnnnnngg cggtggcgga    60
tcc                                                                 63

<210> SEQ ID NO 55
<211> LENGTH: 63
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: k is g or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: k is g or t
<220> FEATURE:

```
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: k is g or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (30)..(30)
<223> OTHER INFORMATION: k is g or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (33)..(33)
<223> OTHER INFORMATION: k is g or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (36)..(36)
<223> OTHER INFORMATION: k is g or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (39)..(39)
<223> OTHER INFORMATION: k is g or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t

<400> SEQUENCE: 55
attttcgtga aaaccnnknn knnknnknnk nnknnknnkn nknnknnkac catcaccctc      60
gag                                                                   63
```

```
<210> SEQ ID NO 56
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: k is g or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: k is g or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: k is g or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (30)..(30)
<223> OTHER INFORMATION: k is g or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (33)..(33)
<223> OTHER INFORMATION: k is g or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (36)..(36)
<223> OTHER INFORMATION: k is g or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (39)..(39)
<223> OTHER INFORMATION: k is g or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
```

```
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t

<400> SEQUENCE: 56
attttcgtga aaaccnnknn knnknnknnk nnknnknnkn nknnknnknn kaccatcacc    60
ctcgag                                                               66

<210> SEQ ID NO 57
<211> LENGTH: 69
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: k is g or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: k is g or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: k is g or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (30)..(30)
<223> OTHER INFORMATION: k is g or t
<220> FEATURE:
<221> NAME/KEY: misc_feature
```

```
<222> LOCATION: (31)..(32)
<223> OTHER INFORMATION: n is a, c, g, or t
<220> FEATURE:
<221> NAME/KEY: misc_feature
<222> LOCATION: (33)..(33)
<223> OTHER INFORMATION: k is g or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (36)..(36)
<223> OTHER INFORMATION: k is g or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (39)..(39)
<223> OTHER INFORMATION: k is g or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t

<400> SEQUENCE: 57
attttcgtga aaaccnnknn knnknnknnk nnknnknnkn nknnknnknn knnkaccatc    60
accctcgag                                                          69

<210> SEQ ID NO 58
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(51)
```

<223> OTHER INFORMATION: n is a, c, g, or t

<400> SEQUENCE: 58

```
attttcgtga aaaccnnnnn nnnnnnnnnn nnnnnnnnnn naccatcacc    60
ctcgag                                                    66
```

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

```
Gln Phe Lys Leu Thr Gly Lys Thr Thr
1               5
```

<210> SEQ ID NO 60
<211> LENGTH: 6
<212> TYPE: PRT
<213> ORGANISM: Artificial Sequence
<220> FEATURE:
<223> OTHER INFORMATION: Synthetic Construct

<400> SEQUENCE: 60

```
Arg Ile Ala Gly Lys Gln
1               5
```

<210> SEQ ID NO 61
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(14)
<223> OTHER INFORMATION: Xaa can be any naturally occurring amino acid

<400> SEQUENCE: 61

```
Gln Lys Glu Thr His Val Leu Arg Leu Arg Gly Xaa Xaa Xaa
1               5                   10
```

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct

<400> SEQUENCE: 62

```
Gln Phe Lys Gly Ala Arg Thr Ala Thr
1               5
```

<210> SEQ ID NO 63
<211> LENGTH: 6
<212> TYPE: PRT
<213> ORGANISM: Artificial Sequence
<220> FEATURE:
<223> OTHER INFORMATION: Synthetic Construct

<400> SEQUENCE: 63

```
Ile Ile Ser Arg Lys Leu
1               5
```

<210> SEQ ID NO 64

```
<211> LENGTH: 14
<212> TYPE: PRT
<213> ORGANISM: Artificial Sequence
<220> FEATURE:
<223> OTHER INFORMATION: Synthetic Construct

<400> SEQUENCE: 64

His Arg Glu Thr Arg Val Leu Ile Phe Arg Gly Asn Glu Ser
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Gln Phe Lys Gly Thr Val Thr Asn Ile
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic Construct

<400> SEQUENCE: 66

Thr Ile Ala Gly Lys Gln
1               5

<210> SEQ ID NO 67
<211> LENGTH: 14
<212> TYPE: PRT
<213> ORGANISM: Artificial Sequence
<220> FEATURE:
<223> OTHER INFORMATION: Synthetic Construct

<400> SEQUENCE: 67

Glu Lys Glu Ser Arg Val Leu Arg Phe Gly Gly Leu Thr Ala
1               5                   10

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

His Leu Lys Gly Thr Val Thr Thr Thr
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Construct

<400> SEQUENCE: 69

Ile Val Tyr Gly Lys Gln
1               5

<210> SEQ ID NO 70
<211> LENGTH: 14
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: Xaa can be any naturally occurring amino acid

<400> SEQUENCE: 70

Gln Lys Glu Thr Gln Leu Leu Arg Phe Leu Gly Xaa Arg Pro
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Synthetic Construct

<400> SEQUENCE: 71

Lys Gly Ala Gly Thr Asn Thr
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Construct

<400> SEQUENCE: 72

Ile Ile Ser Gly Lys Leu
1               5

<210> SEQ ID NO 73
<211> LENGTH: 14
<212> TYPE: PRT
<213> ORGANISM: Artificial Sequence
<220> FEATURE:
<223> OTHER INFORMATION: Synthetic Construct

<400> SEQUENCE: 73

His Arg Glu Thr Arg Val Leu Ile Phe Arg Gly Asn Glu Ala
1               5                   10

<210> SEQ ID NO 74
<211> LENGTH: 4
<212> TYPE: PRT
<213> ORGANISM: Artificial Sequence
<220> FEATURE:
<223> OTHER INFORMATION: Synthetic Construct

<400> SEQUENCE: 74

Lys Thr Ala Ala
1

<210> SEQ ID NO 75
<211> LENGTH: 7
<212> TYPE: PRT
<213> ORGANISM: Artificial Sequence
<220> FEATURE:
<223> OTHER INFORMATION: Synthetic Construct

<400> SEQUENCE: 75

Glu Ile Ile Ser Arg Lys Leu
1               5
```

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct

<400> SEQUENCE: 76

Thr Arg Val Leu Ile Phe Arg Gly Gly
1               5

<210> SEQ ID NO 77
<211> LENGTH: 4
<212> TYPE: PRT
<213> ORGANISM: Artificial Sequence
<220> FEATURE:
<223> OTHER INFORMATION: Synthetic Construct

<400> SEQUENCE: 77

Lys Thr Ala Ala
1

<210> SEQ ID NO 78
<211> LENGTH: 7
<212> TYPE: PRT
<213> ORGANISM: Artificial Sequence
<220> FEATURE:
<223> OTHER INFORMATION: Synthetic Construct

<400> SEQUENCE: 78

Glu Ile Ile Ser Arg Lys Leu
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

Thr Arg Val Leu Ile Phe Arg Gly Asn
1               5

<210> SEQ ID NO 80
<211> LENGTH: 4
<212> TYPE: PRT
<213> ORGANISM: Artificial Sequence
<220> FEATURE:
<223> OTHER INFORMATION: Synthetic Construct

<400> SEQUENCE: 80

Lys Thr Ala Gly
1

<210> SEQ ID NO 81
<211> LENGTH: 7
<212> TYPE: PRT
<213> ORGANISM: Artificial Sequence
<220> FEATURE:
<223> OTHER INFORMATION: Synthetic Construct

<400> SEQUENCE: 81

Glu Val Ile Ser Arg Lys Arg
1               5

```
<210> SEQ ID NO 82
<211> LENGTH: 9
<212> TYPE: PRT
<213> ORGANISM: Artificial Sequence
<220> FEATURE:
<223> OTHER INFORMATION: Synthetic Construct

<400> SEQUENCE: 82

Thr Arg Val Leu Val Phe Gly Arg Arg
1               5

<210> SEQ ID NO 83
<211> LENGTH: 4
<212> TYPE: PRT
<213> ORGANISM: Artificial Sequence
<220> FEATURE:
<223> OTHER INFORMATION: Synthetic Construct

<400> SEQUENCE: 83

Lys Thr Ala Gly
1

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct

<400> SEQUENCE: 84

Glu Ile Ile Ser Arg Lys Arg
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct

<400> SEQUENCE: 85

Thr Arg Val Leu Ile Phe Pro Ser Gly
1               5

<210> SEQ ID NO 86
<211> LENGTH: 4
<212> TYPE: PRT
<213> ORGANISM: Artificial Sequence
<220> FEATURE:
<223> OTHER INFORMATION: Synthetic Construct

<400> SEQUENCE: 86

Lys Thr Ala Gly
1

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct

<400> SEQUENCE: 87

Glu Arg Ile Ala Gly Arg Arg
1               5

<210> SEQ ID NO 88
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

Thr Arg Val Tyr Val Phe Arg Arg Gly
1               5

<210> SEQ ID NO 89
<211> LENGTH: 4
<212> TYPE: PRT
<213> ORGANISM: Artificial Sequence
<220> FEATURE:
<223> OTHER INFORMATION: Synthetic Construct

<400> SEQUENCE: 89

Lys Thr Ala Ala
1

<210> SEQ ID NO 90
<211> LENGTH: 7
<212> TYPE: PRT
<213> ORGANISM: Artificial Sequence
<220> FEATURE:
<223> OTHER INFORMATION: Synthetic Construct

<400> SEQUENCE: 90

Glu Arg Ile Ala Gly Lys Leu
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Construct

<400> SEQUENCE: 91

Thr Arg Val Trp Phe Leu Arg Phe Val
1               5

<210> SEQ ID NO 92
<211> LENGTH: 4
<212> TYPE: PRT
<213> ORGANISM: Artificial Sequence
<220> FEATURE:
<223> OTHER INFORMATION: Synthetic Construct

<400> SEQUENCE: 92

Lys Thr Ala Gly
1

<210> SEQ ID NO 93
<211> LENGTH: 7
<212> TYPE: PRT
<213> ORGANISM: Artificial Sequence
<220> FEATURE:
<223> OTHER INFORMATION: Synthetic Construct

<400> SEQUENCE: 93

Glu Ile Ile Ser Arg Lys Arg
1               5

<210> SEQ ID NO 94
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 94

Thr Arg Val Met Val Phe Ser Lys Gly
1               5

<210> SEQ ID NO 95
<211> LENGTH: 4
<212> TYPE: PRT
<213> ORGANISM: Artificial Sequence
<220> FEATURE:
<223> OTHER INFORMATION: Synthetic Construct

<400> SEQUENCE: 95

Lys Thr Thr Gly
1

<210> SEQ ID NO 96
<211> LENGTH: 7
<212> TYPE: PRT
<213> ORGANISM: Artificial Sequence
<220> FEATURE:
<223> OTHER INFORMATION: Synthetic Construct

<400> SEQUENCE: 96

Glu Val Leu Ser Arg Lys Val
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Construct

<400> SEQUENCE: 97

Thr Arg Val Trp Leu Leu Arg Arg Gly
1               5

<210> SEQ ID NO 98
<211> LENGTH: 4
<212> TYPE: PRT
<213> ORGANISM: Artificial Sequence
<220> FEATURE:
<223> OTHER INFORMATION: Synthetic Construct

<400> SEQUENCE: 98

Lys Thr Ala Ala
1

<210> SEQ ID NO 99
<211> LENGTH: 7
<212> TYPE: PRT
<213> ORGANISM: Artificial Sequence
<220> FEATURE:
<223> OTHER INFORMATION: Synthetic Construct

<400> SEQUENCE: 99

Gly Val Ile Ser Lys Lys Arg
1               5

<210> SEQ ID NO 100
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 100

Thr Arg Val Leu Ile Phe Arg Arg Gly
1               5

<210> SEQ ID NO 101
<211> LENGTH: 4
<212> TYPE: PRT
<213> ORGANISM: Artificial Sequence
<220> FEATURE:
<223> OTHER INFORMATION: Synthetic Construct

<400> SEQUENCE: 101

Lys Thr Ala Ala
1

<210> SEQ ID NO 102
<211> LENGTH: 7
<212> TYPE: PRT
<213> ORGANISM: Artificial Sequence
<220> FEATURE:
<223> OTHER INFORMATION: Synthetic Construct

<400> SEQUENCE: 102

Glu Arg Ile Ala Gly Lys Arg
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic Construct

<400> SEQUENCE: 103

Thr Arg Val Leu Leu Phe Arg Arg Glu
1               5

<210> SEQ ID NO 104
<211> LENGTH: 4
<212> TYPE: PRT
<213> ORGANISM: Artificial Sequence
<220> FEATURE:
<223> OTHER INFORMATION: Synthetic Construct

<400> SEQUENCE: 104

Lys Thr Ser Gly
1

<210> SEQ ID NO 105
<211> LENGTH: 7
<212> TYPE: PRT
<213> ORGANISM: Artificial Sequence
<220> FEATURE:
<223> OTHER INFORMATION: Synthetic Construct

<400> SEQUENCE: 105

Gly Ile Leu Ser Arg Lys Arg
1               5

<210> SEQ ID NO 106
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 106

Thr Arg Val Leu Ile Phe Ser Gly Ala
1               5

<210> SEQ ID NO 107
<211> LENGTH: 4
<212> TYPE: PRT
<213> ORGANISM: Artificial Sequence
<220> FEATURE:
<223> OTHER INFORMATION: Synthetic Construct

<400> SEQUENCE: 107

Lys Thr Ala Ala
1

<210> SEQ ID NO 108
<211> LENGTH: 7
<212> TYPE: PRT
<213> ORGANISM: Artificial Sequence
<220> FEATURE:
<223> OTHER INFORMATION: Synthetic Construct

<400> SEQUENCE: 108

Asp Val Leu Arg Arg Lys Lys
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Construct

<400> SEQUENCE: 109

Thr Arg Leu Trp Ile Val Arg Arg Gly
1               5

<210> SEQ ID NO 110
<211> LENGTH: 4
<212> TYPE: PRT
<213> ORGANISM: Artificial Sequence
<220> FEATURE:
<223> OTHER INFORMATION: Synthetic Construct

<400> SEQUENCE: 110

Lys Thr Ala Gly
1

<210> SEQ ID NO 111
<211> LENGTH: 7
<212> TYPE: PRT
<213> ORGANISM: Artificial Sequence
<220> FEATURE:
<223> OTHER INFORMATION: Synthetic Construct

<400> SEQUENCE: 111

Glu Ile Ile Ser His Met Arg
1               5

<210> SEQ ID NO 112
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 112

Thr Arg Val Leu Ile Phe Ser Gly Gly
1               5

<210> SEQ ID NO 113
<211> LENGTH: 4
<212> TYPE: PRT
<213> ORGANISM: Artificial Sequence
<220> FEATURE:
<223> OTHER INFORMATION: Synthetic Construct

<400> SEQUENCE: 113

Lys Thr Ala Gly
1

<210> SEQ ID NO 114
<211> LENGTH: 7
<212> TYPE: PRT
<213> ORGANISM: Artificial Sequence
<220> FEATURE:
<223> OTHER INFORMATION: Synthetic Construct

<400> SEQUENCE: 114

Gly Ile Leu Ser Arg Lys Pro
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic Construct

<400> SEQUENCE: 115

Thr Arg Val Val Val Phe Arg Arg Gly
1               5

<210> SEQ ID NO 116
<211> LENGTH: 4
<212> TYPE: PRT
<213> ORGANISM: Artificial Sequence
<220> FEATURE:
<223> OTHER INFORMATION: Synthetic Construct

<400> SEQUENCE: 116

Lys Thr Ala Gly
1

<210> SEQ ID NO 117
<211> LENGTH: 7
<212> TYPE: PRT
<213> ORGANISM: Artificial Sequence
<220> FEATURE:
<223> OTHER INFORMATION: Synthetic Construct

<400> SEQUENCE: 117

Gly Arg Ile Ala Gly Lys Arg
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 118

Ser Arg Val Leu Ile Phe Arg Gly Gly
1               5

<210> SEQ ID NO 119
<211> LENGTH: 4
<212> TYPE: PRT
<213> ORGANISM: Artificial Sequence
<220> FEATURE:
<223> OTHER INFORMATION: Synthetic Construct

<400> SEQUENCE: 119

Lys Thr Ala Ala
1

<210> SEQ ID NO 120
<211> LENGTH: 7
<212> TYPE: PRT
<213> ORGANISM: Artificial Sequence
<220> FEATURE:
<223> OTHER INFORMATION: Synthetic Construct

<400> SEQUENCE: 120

Glu Arg Ile Ser Arg Lys Arg
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic Construct

<400> SEQUENCE: 121

Thr Arg Val Leu Leu Phe Pro Gly Gly
1               5

<210> SEQ ID NO 122
<211> LENGTH: 12
<212> TYPE: PRT
<213> ORGANISM: Artificial Sequence
<220> FEATURE:
<223> OTHER INFORMATION: Synthetic Construct

<400> SEQUENCE: 122

Leu Leu Pro Lys Glu Leu Ala Leu Tyr Val Leu Ser
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthetic Construct

<400> SEQUENCE: 123

Leu Leu Pro Leu Glu Leu Ser Phe Tyr Leu Leu Lys
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 124

Ser Leu Pro Asp Glu Leu Leu Leu Gly Ile Ser Phe
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic Construct

<400> SEQUENCE: 125

Leu Leu Pro Asp Ser Leu Val Tyr Gln Ile Phe Leu
1               5                   10

<210> SEQ ID NO 126
<211> LENGTH: 16
<212> TYPE: PRT
<213> ORGANISM: Artificial Sequence
<220> FEATURE:
<223> OTHER INFORMATION: Synthetic Construct

<400> SEQUENCE: 126

Ala Leu Pro Ala Arg Gly Leu Asp His Ile Ala Glu Asn Ile Leu Ser
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Synthetic Construct

<400> SEQUENCE: 127

Ala Leu Pro Glu Gln Gly Leu Asp His Ile Ala Glu Asn Ile Leu Ser
1               5                   10                  15

<210> SEQ ID NO 128
<211> LENGTH: 12
<212> TYPE: PRT
<213> ORGANISM: Artificial Sequence
<220> FEATURE:
<223> OTHER INFORMATION: Synthetic Construct

<400> SEQUENCE: 128

Arg Leu Pro Asp Leu Ala Leu Lys Arg Ile Phe Ser
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Synthetic Construct

<400> SEQUENCE: 129

Tyr Pro Tyr Lys Ser Gly Ser Tyr His Asn Asn Tyr
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Synthetic Construct

<400> SEQUENCE: 130
```

Tyr Pro Tyr Lys Tyr Gly Thr Tyr His His Asn Tyr
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic Construct

<400> SEQUENCE: 131

Tyr Pro Tyr Lys Ser Gly Thr Phe His Asn Asn Tyr
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetic Construct

<400> SEQUENCE: 132

Tyr Pro Tyr Lys Tyr Gly Ser Tyr His Asn Asn Tyr
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Synthetic Construct

<400> SEQUENCE: 133

Tyr Pro Tyr Lys Ser Gly Thr Tyr His Asn Asn Tyr
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic Construct

<400> SEQUENCE: 134

Tyr Pro Tyr Lys Ser Gly Thr Phe His Asp Asn Tyr
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct

<400> SEQUENCE: 135

Gln Phe Lys Thr Leu Thr Gly Lys Thr Thr
1               5                   10

<210> SEQ ID NO 136
<211> LENGTH: 7
<212> TYPE: PRT
<213> ORGANISM: Artificial Sequence
<220> FEATURE:
<223> OTHER INFORMATION: Synthetic Construct

<400> SEQUENCE: 136

```
Glu Arg Ile Ala Gly Lys Gln
1               5

<210> SEQ ID NO 137
<211> LENGTH: 12
<212> TYPE: PRT
<213> ORGANISM: Artificial Sequence
<220> FEATURE:
<223> OTHER INFORMATION: Synthetic Construct

<400> SEQUENCE: 137

Gln Lys Glu Thr His Val Leu Arg Leu Arg Gly Gly
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(14)
<223> OTHER INFORMATION: Xaa can be any naturally occurring amino acid

<400> SEQUENCE: 138

Gln Lys Glu Thr His Val Leu Arg Leu Arg Gly Xaa Xaa Xaa
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Synthetic Construct

<400> SEQUENCE: 139

Gln Phe Lys Thr Gly Ala Arg Thr Ala Thr
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Synthetic Construct

<400> SEQUENCE: 140

Glu Ile Ile Ser Arg Lys Leu
1               5

<210> SEQ ID NO 141
<211> LENGTH: 14
<212> TYPE: PRT
<213> ORGANISM: Artificial Sequence
<220> FEATURE:
<223> OTHER INFORMATION: Synthetic Construct

<400> SEQUENCE: 141

His Arg Glu Thr Arg Val Leu Ile Phe Arg Gly Asn Glu Ser
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 142

Gln Lys Glu Thr Arg Val Leu Ile Phe Arg Gly Gly
1               5                   10

<210> SEQ ID NO 143
<211> LENGTH: 8
<212> TYPE: PRT
<213> ORGANISM: Artificial Sequence
<220> FEATURE:
<223> OTHER INFORMATION: Synthetic Construct

<400> SEQUENCE: 143

Gln Phe Lys Thr Gly Ala Arg Thr
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic Construct

<400> SEQUENCE: 144

Glu Val Ile Ser Arg Lys Arg
1               5

<210> SEQ ID NO 145
<211> LENGTH: 12
<212> TYPE: PRT
<213> ORGANISM: Artificial Sequence
<220> FEATURE:
<223> OTHER INFORMATION: Synthetic Construct

<400> SEQUENCE: 145

Gln Lys Glu Thr Arg Val Leu Val Phe Gly Arg Arg
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(15)
<223> OTHER INFORMATION: Xaa can be any naturally occurring amino acid

<400> SEQUENCE: 146

Gln Phe Lys Thr Xaa Xaa Xaa Xaa Xaa Xaa Xaa Xaa Xaa Xaa Xaa
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(16)
<223> OTHER INFORMATION: Xaa can be any naturally occurring amino acid

<400> SEQUENCE: 147

Gln Phe Lys Thr Xaa Xaa Xaa Xaa Xaa Xaa Xaa Xaa Xaa Xaa Xaa Xaa
1               5                   10                  15
```

<210> SEQ ID NO 148
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(17)
<223> OTHER INFORMATION: Xaa can be any naturally occurring amino acid

<400> SEQUENCE: 148

Gln Phe Lys Thr Xaa Xaa Xaa Xaa Xaa Xaa Xaa Xaa Xaa Xaa Xaa Xaa
1               5                   10                  15

Xaa

<210> SEQ ID NO 149
<211> LENGTH: 16
<212> TYPE: PRT
<213> ORGANISM: Artificial Sequence
<220> FEATURE:
<223> OTHER INFORMATION: Synthetic Construct

<400> SEQUENCE: 149

Gln Phe Lys Thr Tyr Pro Tyr Lys Tyr Gly Thr Tyr His His Asn Tyr
1               5                   10                  15

<210> SEQ ID NO 150
<211> LENGTH: 46
<212> TYPE: PRT
<213> ORGANISM: Artificial Sequence
<220> FEATURE:
<223> OTHER INFORMATION: Synthetic Construct

<400> SEQUENCE: 150

Asp Asp Glu Gly Asp Asp Asp Pro Val Pro Leu Pro Asn Val Asn Ala
1               5                   10                  15

Ala Ile Leu Lys Lys Val Ile Gln Trp Cys Thr His His Lys Asp Asp
            20                  25                  30

Pro Pro Pro Pro Glu Asp Asp Glu Asn Lys Glu Lys Arg Thr
        35                  40                  45

<210> SEQ ID NO 151
<211> LENGTH: 32
<212> TYPE: PRT
<213> ORGANISM: Artificial Sequence
<220> FEATURE:
<223> OTHER INFORMATION: Synthetic Construct

<400> SEQUENCE: 151

Asp Pro Val Pro Leu Pro Asn Val Asn Ala Ala Ile Leu Lys Lys Val
1               5                   10                  15

Ile Gln Trp Cys Thr His His Lys Asp Asp Pro Gly Gly Ser Gly Thr
            20                  25                  30

<210> SEQ ID NO 152
<211> LENGTH: 40
<212> TYPE: PRT
<213> ORGANISM: Artificial Sequence
<220> FEATURE:
<223> OTHER INFORMATION: Synthetic Construct

<400> SEQUENCE: 152

Asp Pro Val Pro Leu Pro Asn Val Asn Ala Ala Ile Leu Lys Lys Val
1               5                   10                  15

```
Ile Gln Trp Cys Thr His His Lys Asp Asp Pro Pro Pro Glu Asp
        20                  25                  30

Asp Glu Asn Lys Glu Lys Arg Thr
        35                  40
```

<210> SEQ ID NO 153
<211> LENGTH: 38
<212> TYPE: PRT
<213> ORGANISM: Artificial Sequence
<220> FEATURE:
<223> OTHER INFORMATION: Synthetic Construct

<400> SEQUENCE: 153

```
Asp Asp Glu Gly Asp Asp Asp Pro Val Pro Leu Pro Asn Val Asn Ala
1               5                   10                  15

Ala Ile Leu Lys Lys Val Ile Gln Trp Cys Thr His His Lys Asp Asp
            20                  25                  30

Pro Gly Gly Ser Gly Thr
        35
```

<210> SEQ ID NO 154
<211> LENGTH: 12
<212> TYPE: PRT
<213> ORGANISM: Artificial Sequence
<220> FEATURE:
<223> OTHER INFORMATION: Synthetic Construct

<400> SEQUENCE: 154

```
Tyr Pro Tyr Lys Ser Gly Ser Tyr His Asn Asn Tyr
1               5                   10
```

<210> SEQ ID NO 155
<211> LENGTH: 12
<212> TYPE: PRT
<213> ORGANISM: Artificial Sequence
<220> FEATURE:
<223> OTHER INFORMATION: Synthetic Construct

<400> SEQUENCE: 155

```
Tyr Pro Tyr Lys Tyr Gly Thr Tyr His His Asn Tyr
1               5                   10
```

<210> SEQ ID NO 156
<211> LENGTH: 12
<212> TYPE: PRT
<213> ORGANISM: Artificial Sequence
<220> FEATURE:
<223> OTHER INFORMATION: Synthetic Construct

<400> SEQUENCE: 156

```
Tyr Pro Tyr Lys Ser Gly Thr Phe His Asn Asn Tyr
1               5                   10
```

<210> SEQ ID NO 157
<211> LENGTH: 12
<212> TYPE: PRT
<213> ORGANISM: Artificial Sequence
<220> FEATURE:
<223> OTHER INFORMATION: Synthetic Construct

<400> SEQUENCE: 157

```
Tyr Pro Tyr Lys Tyr Gly Ser Tyr His Asn Asn Tyr
1               5                   10
```

```
<210> SEQ ID NO 158
<211> LENGTH: 12
<212> TYPE: PRT
<213> ORGANISM: Artificial Sequence
<220> FEATURE:
<223> OTHER INFORMATION: Synthetic Construct

<400> SEQUENCE: 158

Tyr Pro Tyr Lys Ser Gly Thr Tyr His Asn Asn Tyr
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Synthetic Construct

<400> SEQUENCE: 159

Tyr Pro Tyr Lys Ser Gly Thr Phe His Asp Asn Tyr
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Synthetic Construct

<400> SEQUENCE: 160

Tyr Pro Tyr Lys Ser Gly Thr Tyr His His Asn Tyr
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Synthetic Construct

<400> SEQUENCE: 161

Tyr Pro Tyr Lys Tyr Gly Thr Tyr His Asn Asn Tyr
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Synthetic Construct

<400> SEQUENCE: 162

Tyr Pro Tyr Lys Ser Gly Ser Phe His Asn Asn Tyr
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Synthetic Construct

<400> SEQUENCE: 163

Tyr Pro Tyr Lys Ser Gly Ser Tyr His His Asn Tyr
1               5                   10

<210> SEQ ID NO 164
```

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 164

Tyr Pro Tyr Lys Ser Gly Asn Phe His Asn Asn Tyr
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic Construct

<400> SEQUENCE: 165

Tyr Pro Tyr Lys Ser Gly Ser Tyr His Asp Asn Tyr
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Synthetic Construct

<400> SEQUENCE: 166

Tyr Pro Tyr Lys His Gly Ser Tyr His Asn Asn Tyr
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Synthetic Construct

<400> SEQUENCE: 167

Tyr Pro Tyr Lys Tyr Gly Ser Phe His Asn Asn Tyr
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Synthetic Construct

<400> SEQUENCE: 168

Tyr Pro Tyr Arg Ser Gly Thr Tyr His Asn Asn Tyr
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Synthetic Construct

<400> SEQUENCE: 169

Tyr Pro Tyr Lys Thr Gly Ser Tyr His Asn Asn Tyr
1               5                   10

<210> SEQ ID NO 170
<211> LENGTH: 12
```

```
<212> TYPE: PRT
<213> ORGANISM: Artificial Sequence
<220> FEATURE:
<223> OTHER INFORMATION: Synthetic Construct

<400> SEQUENCE: 170

Tyr Pro Tyr Lys Ala Gly Ser Tyr His Asn Asn Tyr
1               5                   10
```